(12) United States Patent
Freeman et al.

(10) Patent No.: US 6,242,238 B1
(45) Date of Patent: Jun. 5, 2001

(54) ISOLATED NUCLEIC ACID MOLECULE ENCODING MAMMALIAN ENDOGLUCURONIDASE AND USES THEREFOR

(75) Inventors: Craig Geoffrey Freeman, Rivett; Mark Darren Hulett, Cook; Christopher Richard Parish, Campbell; Brenton James Hamdorf, Swinger Hill, all of (AU)

(73) Assignee: The Australian National University, Acton (AU)

( * ) Notice: Subject to any disclaimer, the term of this patent is extended or adjusted under 35 U.S.C. 154(b) by 0 days.

(21) Appl. No.: 09/181,336

(22) Filed: Oct. 28, 1998

(30) Foreign Application Priority Data

Oct. 28, 1997 (AT) ........................................ 0062/97
Dec. 9, 1997 (AT) ........................................ 0812/97

(51) Int. Cl.⁷ ............................... C12N 9/24; C12N 1/20; C12N 15/00; C07H 21/02
(52) U.S. Cl. .................. 435/200; 435/252.3; 435/320.1; 536/23.1; 536/23.2
(58) Field of Search ................................ 435/6, 200, 232, 435/7.4, 94.5, 252.3, 320.1; 536/23.2

(56) References Cited

U.S. PATENT DOCUMENTS 5,968,822 * 10/1999 Pecker et al. ................... 435/325

FOREIGN PATENT DOCUMENTS

WO91/19197 12/1991 (WO).
WO 95/04158 * 2/1995 (WO).
WO98/03638 1/1998 (WO).
WO99/11798 3/1999 (WO).

OTHER PUBLICATIONS

Turnbull, J.E. and Gallagher. J.T. (1990), "Molecular organization of heparan sulphate from human skin fibroblasts", *Biochem. J.* 265:715–724.

Turnbull J.E. and Gallagher, J.T. (1991), "Distribution of iduronate 2–sulphate residues in heparan sulphate", *Biochem. J.* 273:553–559.

Freeman, C. and Parish, C.R. (1997) "A rapid quantitative assay for the detection of mammalian heparanase activity", *Biochem. J.* 325:229–237.

Parish, C. et al., (1999) "Identification of sulfated oligosaccharide–based inhibitors of tumor growth and metastasis using novel in vitro assays for angiogenesis and heparanase activity" *Cancer Research* 59:3433–3441.

Gilat, D. et al. (1995), "Molecular behavior adapts to context: Heparanase functions as an extracellular matrix–degrading enzyme or as a T cell adhesion molecule, depending on the local pH," *J. Exp. Med.* 181: 1929–1934.

Graham, L.D. and Underwood, P.A. (1996), "Comparison of the heparanase enzymes from mouse melanoma cells, mouse macrophages and human platelets" *Biochem. Mol. Biol. Int.* 39: 563–571.

* cited by examiner

*Primary Examiner*—Ponnathapu Achutamurthy
*Assistant Examiner*—Manjunath N. Rao
(74) *Attorney, Agent, or Firm*—Burns, Doane, Swecker & Mathis, LLP

(57) ABSTRACT

The present invention relates to isolated or recombinant mammalian endoglucuronidase enzymes, polypeptides and peptides, in particular human, murine and rat heparanases, genetic sequences encoding same and uses therefor, for example in the determination and characterisation of chemical compounds, proteins, polypeptides, small molecules and macromolecules capable of inhibiting metastasis, angiogenesis, angioplasty-induced restenosis, atherosclerosis, inflammation, promote wound healing and otherwise modulate physiological processes involving heparanase cleavage of heparan sulphate. The invention further relates to a method of altering, modifying or otherwise modulating the level of expression of mammalian heparanase in a cell. A further aspect of the invention relates to immunoreactive molecules capable of binding to and/or inhibiting mammalian heparanase, in particular monoclonal antibodies. A still further aspect of the invention contemplates the use of heparanase as an agent to promote the processes of wound healing.

36 Claims, 5 Drawing Sheets

FIG. 6

ISOLATED NUCLEIC ACID MOLECULE ENCODING MAMMALIAN ENDOGLUCURONIDASE AND USES THEREFOR

FIELD OF THE INVENTION

The invention relates to isolated or recombinant mammalian endoglucuronidase enzymes, polypeptides and peptides, in particular human platelet heparanase, genetic sequences encoding the same and uses therefor, for example in the determination and characterisation of chemical compounds, proteins, polypeptides, small molecules and macromolecules capable of inhibiting metastasis, angiogenesis, angioplasty-induced restenosis, atherosclerosis, inflammation, promote wound healing and otherwise modulate physiological processes involving heparanase cleavage of heparan sulphate. The invention further relates to a method of altering, modifying or otherwise modulating the level of expression of mammalian heparanase in a cell. A further aspect of the invention relates to immunoreactive molecules capable of binding to and/or inhibiting mammalian heparanase, in particular monoclonal antibodies. A still further aspect of the invention contemplates the use of heparanase as an agent to inhibit the processes of neovascularisation.

GENERAL

Bibliographic details of the publications numerically referred to in this specification are collected at the end of the description.

This specification contains nucleotide and amino acid sequence information prepared using the programme PatentIn Version 2.0, presented herein after the bibliography. Each nucleotide or amino acid sequence is identified in the sequence listing by the numeric indicator <210> followed by the sequence identifier (e.g. <210>1, <210>2, etc). The length, type of sequence (DNA, protein (PRT), etc) and source organism for each nucleotide or amino acid sequence are indicated by information provided in the numeric indicator fields <211>, <212> and <213>, respectively. Nucleotide and amino acid sequences referred to in the specification are defined by the information provided in numeric indicator field <400> followed by the sequence identifier (eg. <400>1, <400>2, etc).

The designation of nucleotide residues referred to herein are those recommended by the IUPAC-IUB Biochemical Nomenclature Commission, wherein A represents Adenine, C represents Cytosine, G represents Guanine, T represents thymine, Y represents a pyrimidine residue, R represents a purine residue, M represents Adenine or Cytosine, K represents Guanine or Thymine, S represents Guanine or Cytosine, W represents Adenine or Thymine, H represents a nucleotide other than Guanine, B represents a nucleotide other than Adenine, V represents a nucleotide other than Thymine, D represents a nucleotide other than Cytosine and N represents any nucleotide residue.

The designations for amino acid residues referred to herein are set forth in Table I.

As used herein the term "derived from" shall be taken to indicate that a specified integer may be obtained from a particular source albeit not necessarily directly from that source.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

BACKGROUND OF THE INVENTION

Tissue invasion by blood-borne malignant tumour cells and leukocytes involves their adhesion to the luminal surface of the vascular endothelium, passage through the vascular endothelial cell layer and the subsequent degradation of the underlying basal lamina and extracellular matrix (ECM) with a battery of secreted and/or cell surface protease and glycosidase activities (Nakajima et al., 1983; Schmitt et al., 1992; Vlodavsky et al., 1992).

Studies have shown that while the initial entrapment of metastatic tumour cells by the capillary endothelium is platelet-independent, platelet aggregation which occurs shortly thereafter can lead to platelet activation and degranulation, resulting in gap formation and retraction of endothelial cells, exposing the underlying basement membrane to adhesion by the tumour cells (Tanaka et al., 1986; Crissman et al., 1985; Yahalom et al., 1985).

The basal lamina and underlying connective tissue stroma consist predominantly of a complex network of fibronectin, laminin, collagen type IV and vitronectin, each of which interact with heparan sulphate (HS) side chains of heparan sulphate proteoglycans (HSPG) embedded with the matrix (Yurchenco and Schittny, 1990).

HS chains generally consist of clusters of sulphated disaccharide units (predominantly N-sulphated glucosamine linked 1–4 to $\alpha$-L-iduronic acid residues) separated by lowly or non-sulphated regions (predominantly disaccharide units of N-acetylated glucosamine linked 1–4 to $\beta$-D-glucuronic acid) (Turnbull and Gallagher, 1990; 1991).

In work leading up to the present invention, the inventors sought to isolate and characterise enzymes, proteins, polypeptides and peptides which are capable of cleaving the HS side chains of HSPG embedded in the matrix and genetic sequences encoding same. The genetic sequences thus derived provide a means for assisting the disassembly of the ECM and facilitating cell migration, when expressed at the matrix site or transported thereto.

The genetic sequences of the present invention further provide the means for developing a wide range of therapeutic and prophylactic pharmaceutical compounds to inhibit metastasis, neovascularisation, angiogenesis, angioplasty-induced restenosis, atherosclerotic plaque formation and inflammation and/or to promote wound healing, amongst others.

SUMMARY OF THE INVENTION

One aspect of the invention provides an isolated nucleic acid molecule comprising a sequence of nucleotides encoding or complementary to a sequence encoding a polypeptide capable of hydrolysing glycosidic bonds in HS.

A second aspect of the invention provides an isolated nucleic acid molecule comprising a sequence of nucleotides which encodes or is complementary to a sequence which encodes a mammalian endoglucuronidase polypeptide, in particular heparanase or fragment or derivative thereof. More particularly, the mammalian endoglucuronidase polypeptide comprises an amino acid sequence as set forth in any one or more <400>1–11 or <400>13 or <400>15 or <400>17 or <400>19 or <400>23 or is at least 40% identical thereto.

A further aspect of the invention provides an isolated nucleic acid molecule which is at least 40% identical to the nucleotide sequence set forth in any one of <400>12 or <400>14 or <400>16 or <400>18 or a homologue, analogue or derivative thereof, or a complementary sequence thereto.

A still further aspect of the present invention provides a genetic construct which expresses a recombinant endoglucuronidase activity, in particular heparanase activity or an active site thereof.

Another aspect of the invention provides a recombinant mammalian endoglucuronidase polypeptide, in particular heparanase or fragment or derivative thereof.

Still yet another aspect of the invention contemplates a method of identifying a modulator of heparanase activity, said method comprising assaying recombinant heparanase activity in the presence of a potential modulator and comparing said activity to the activity of recombinant heparanase in the absence of said potential modulator.

A further aspect of the invention contemplates an inhibitor of a mammalian endoglucuronidase polypeptide, in particular a mammalian heparanase. The inhibitor molecules encompassed by the invention are particularly useful as inhibitors of metastasis, angiogenesis, wound healing, angioplasty-induced restenosis, arteriosclerosis, atherosclerosis, inflammation or other physiological or medical condition wherein heparanase activity is elevated.

In still yet another aspect of the invention there is contemplated the use of recombinant heparanase or an active fragment or derivative thereof to inhibit neovascularisation and its associated processes involved in the regulation of tissue development, inflammation, wound healing and tumour metastasis.

The recombinant polypeptides of the invention are also useful in the sequencing of sulphated molecules such as HSPG and heparan sulphate molecules or to assist in the determination of the structure of sulphated proteoglycans, sulphated oligosaccharides and heparan sulphate molecules, wherein said recombinant polypeptide is used to cleave the heparan sulphate moiety therefrom.

A further aspect of the invention provides an immunologically interactive molecule which is capable of binding to the recombinant endoglucuronidase polypeptide of the invention, in particular an antibody molecule which is capable of binding to and/or inhibiting the catalytic activity of a heparanase polypeptide. The antibody molecules of the invention are particularly useful in the diagnosis of heparanase expression in biological samples, particularly where patients are suspected of having a condition associated with elevated heparanase expression such as cancer, metastasis, angiogenesis, angioplasty-induced restenosis, atherosclerosis or inflammation, amongst others.

A further aspect of the invention provides a recombinant endoglucuronidase polypeptide, in particular a recombinant heparanase polypeptide or an immunologically interactive homologue, analogue or derivative thereof for use as a "standard" in the diagnosis of heparanase expression of biological samples, particularly in diagnostic assays of patient-derived samples such as serum wherein the patients are suspected of having a condition associated with elevated heparanase expression, such as those listed supra.

A still further aspect of the invention contemplates a method of diagnosing elevated heparanase expression in a human or animal subject said method comprising contacting an antibody molecule which is capable of binding to a heparanase polypeptide with a biological sample such as serum or isolated cells derived from said subject for a time and under conditions sufficient for an antibody:antigen complex to form and then detecting and/or quantifying the complex thus formed. Quantification according to this aspect of the invention is performed using a standard protein which comprises recombinant heparanase or a homologue, analogue or derivative thereof.

A still further aspect of the invention contemplates a method of diagnosing elevated heparanase expression in a human or animal subject, said method comprising contacting a biological sample which comprises mRNA encoding heparanase derived from said subject or an isolate mRNA sample encoding heparanase derived from said subject with an isolated nucleic acid molecule which comprises a nucleotide sequence capable of binding to said mRNA encoding heparanase for a time and under conditions sufficient for hybridisation to occur and then detecting and/or quantifying said hybridisation.

BRIEF DESCRIPTION OF THE DRAWINGS

FIG. 6 is a copy of a schematic representation showing an alignment of the human (<400>13), murine (<400>17) and rat (<400>19) heparanase amino acid sequences. The sequences of the human (hu.hep), murine (mu.hep) and rat (rat.hep) heparanase polypeptides were aligned using the PILEUP programme at the Computer Genetics Group (Devereaux et al, 1984). Identical amino acids are boxed. Numbers refer to the amino acid positions for each of the sequence shown in the Figure.

DETAILED DESCRIPTION OF THE PREFERRED EMBODIMENTS

Figure 1:
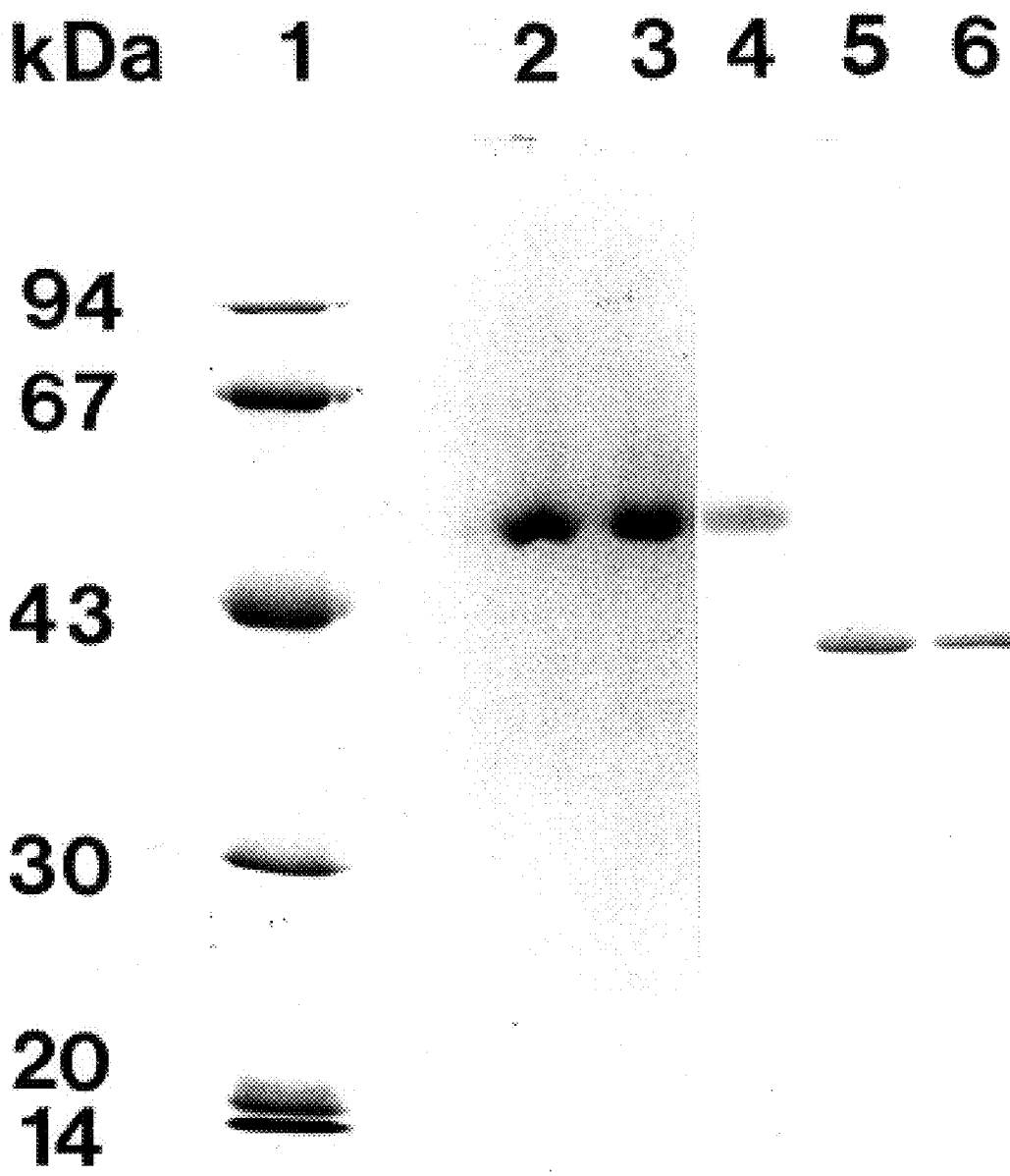
FIG. 1 is a photographic representation of purified human platelet heparanase and of deglycosylated purified human platelet heparanase following SDS-PAGE. Purified platelet heparanase was reduced with dithioerythrietol and electrophoresed on a 10% polyacrylamide gel and stained with Coomassie Brillant Blue R250. Lane 1, Mr standards (phosphorylase b (94 kDa), bovine serum albumin (67 kDa), ovalbumin (43 kDa), carbonic anhydrase (30 kDa), soyabean trypsin inhibitor (20 kDa) and α-lactalbumin (14 kDa)); lane 2, human platelet heparanase and lane 3, membrane-associated human platelet heparanase. Human platelet heparanase was incubated with a) no enzyme (lane 4), b) N-glycosidase F (lane 5) and c) N-glycanase F, O-glycosidase and neuraminidase (lane 6).

One aspect of the present invention provides an isolated nucleic acid molecule which comprises a nucleotide sequence which encodes polypeptide capable of cleaving the HS side chains of HSPG or a complementary nucleotide sequence thereto.

The term "isolated" means that a stated integer or group of integers is provided in a form which is distinct from that which occurs in nature, preferably wherein one or more contaminants have been removed.

As used herein, the term "cleaving" or similar term includes the hydrolysis of one or more glycosidic bonds of HS.

The nucleic acid molecule of the invention may be RNA or DNA (e.g. cDNA), single or double stranded and linear or covalently closed. The nucleic acid molecule may also be genomic DNA corresponding to the entire gene or a substantial portion thereof or to fragments and derivatives thereof. The nucleotide sequence may correspond to the naturally occurring nucleotide sequence or may contain single or multiple nucleotide substitutions, deletions or additions.

More particularly, the isolated nucleic acid molecule may be one or more of the following molecules:
(i) a classical genomic gene consisting of transcriptional and/or translational regulatory sequences and/or a coding region and/or non-translated sequences (i.e. introns, 5'- and 3'-untranslated sequences);
(ii) mRNA or cDNA corresponding to the coding region or a part thereof or one or more exon sequences, and 5'-untranslated sequences and/or 3'-untranslated sequences of the gene;
(iii) a structural region corresponding to the coding region or a part thereof or one or more exon sequences; and/or
(iv) a synthetic or fusion molecule encoding a functional endoglucuronidase polypeptide or heparanase polypeptide or a homologue, analogue or derivative thereof.

In a particularly preferred embodiment of the present invention, the isolated nucleic acid molecule is a cDNA molecule.

As used herein, the term "polypeptide" shall be taken to refer to any polymer which at least comprises amino acids including a non-enzymatically-active peptide molecule or an enzymatically-active protein of enzyme molecule or alternatively, a fusion molecule. A reference to "polypeptides" shall also be taken to include both naturally-occurring molecules and recombinantly-produced molecules.

In a preferred embodiment of the present invention, the polypeptide product of the isolated nucleic acid molecule is an endoglucuronidase polypeptide or a homologue, analogue or derivative thereof.

As used herein, the term "endoglucuronidase" shall be taken to refer to any peptide, polypeptide, protein or enzyme molecule which is at least capable of cleaving a sulphated disaccharide or sulphated polysaccharide from a sulphated proteoglycan molecule.

Those skilled in the art are aware that the endoglucuronidases include both heparanases and endoglycosidases, amongst others which are at least capable of hydrolysing or otherwise cleaving one or more sulphated disaccharide units from proteoglycans. However, not all endoglucuronidases possess high activity on all proteoglycan substrates and some degree of substrate specificity generally occurs for enzymes within this class.

For example, murine melanoma B16 heparanase cleaves both heparin and HS albeit not at equal efficiency (Graham and Underwood, 1996). On the other hand, tumour-derived heparanase is unable to degrade endothelial cell surface HSPG (Hennes et al., 1988), whereas human platelets degrade both endothelial cell surface HSPG, tumour-derived HSPG, ECM-associated HSPC and other structures which are more heparin-like in structure (Hoogewerf et al., 1995; Bartlett et al., 1995 a, b; Yahalom et al., 1984; Castellot Jr. et al., 1982; Wasteson et al., 1976; Wasteson et al., 1977; Gamse et al., 1978), presumably via the heparanase activity therein.

As used herein the term "heparanase" shall be taken to refer to any peptide, polypeptide, protein or enzyme molecule which is at least capable of removing the HS side chain from HSPG associated with the endothelial cell surface and/or the extracellular matrix (ECM) and/or tumour cells and/or heparin, and includes both recombinant molecules, isolated naturally-occurring isoforms and fusion polypeptides.

Preferably, the endoglucuronidase polypeptide is heparanase, or a homologue, analogue or derivative thereof, more preferably heparanase polypeptide which is at least capable of degrading endothelial cell surface HSPG by cleaving the HS side chain(s) therefrom, even more preferably a heparanase polypeptide which is at least capable of degrading both endothelial cell surface HSPG and ECM-associated HSPG and even more preferably a heparanase polypeptide which is at least capable of cleaving endothelial cell surface HSPG, tumour-derived HSPG, ECM-associated HSPG and heparin-like HS side chains, including heparin.

As exemplified herein, the present inventors have isolated the heparanase enzyme from human platelets, determined the N-terminal amino acid sequence and amino acid sequence of tryptic peptides of the heparanase polypeptide and utilised the amino acid sequence to isolate a cDNA molecule which encodes platelet heparanase.

Accordingly, in a particularly preferred embodiment the present invention provides an isolated nucleic acid molecule which encodes or is complementary to an isolated nucleic acid molecule which encodes a heparanase polypeptide which at least comprises an amino acid sequence which is at least 40% identical to the sequence set forth in any one of <400>1–11 or <400>13 or <400>15 or <400>17 or <400>19 or <400>23.

Preferably, the percentage similarity to any one of <400>1–11 or <400>13 or <400>15 or <400>17 or <400>19 or <400>23 is at least about 60%, more preferably at least about 80%, even more preferably at least about 90%.

In determining whether or not two amino acid sequences fall within these percentage limits, those skilled in the art will be aware that it is necessary to conduct a side-by-side comparison or multiple alignment of sequences. In such comparisons or alignments, differences will arise in the positioning of non-identical residues, depending upon the algorithm used to perform the alignment. In the present context, reference to a percentage identity or similarity between two or more amino acid sequences shall be taken to refer to the number of identical and similar residues respectively, between said sequences as determined using any standard algorithm known to those skilled in the art. For example, amino acid sequence identities or similarities may be calculated using the GAP programme and/or aligned using the PILEUP programme of the Computer Genetics Group, Inc., University Research Park, Madison, Wis., United States of America (Devereaux et al, 1984). The GAP programme utilizes the algorithm of Needleman and Wunsch (1970) to maximise the number of identical/similar residues and to minimise the number and/or length of sequence gaps in the alignment. Alternatively or in addition, wherein more than two amino acid sequences are being compared, the ClustalW programme of Thompson et al (1994) is used.

In an alternative embodiment, the isolated nucleic acid molecule of the invention encodes or is complementary to an isolated nucleic acid molecule which encodes a heparanase polypeptide which at least comprises an amino acid sequence which is substantially identical to any one of <400>1–11 or <400>13 or <400>15 or <400>17 or <400>19 or <400>23.

As used herein, the term "substantially identical" or similar term shall be taken to include any sequence which is at least about 95% identical to a stated nucleotide sequence or amino acid sequence, including any homologue, analogue or derivative of said stated nucleotide sequence or amino acid sequence.

For the purposes of nomenclature, the amino acid sequences set forth in <400>1–11 relate to the amino acid sequences of tryptic peptides derived from the purified heparanase polypeptide. The complete amino acid sequence of the human heparanase polypeptide is set forth in <400>13. The amino acid sequence of a human heparanase polypeptide derivative used to produce antibodies suitable for diagnostic applications, described in Example 8, is set forth in <400>23. The complete amino acid sequence of a variant human heparanase polypeptide is set forth in <400>15. The partial amino acid sequence of the murine heparanase polypeptide is set forth in <400>17. The Partial amino acid sequence of the rat heparanase polypeptide is set forth in <400>19.

In the present context, "homologues" of an endoglucuronidase or heparanase polypeptide refer to those polypeptides, enzymes or proteins which have a similar activity to the human heparanase polypeptide and are at least about 40% identical thereto, notwithstanding any amino acid substitutions, additions or deletions. A homologue may be isolated or derived from the same species as the heparanase polypeptide exemplified herein or from a different species. Furthermore, the amino acids of a homologous polypeptide may be replaced by other amino acids having similar properties, for example hydrophobicity, hydrophilicity, hydrophobic moment, charge or antigenicity, and so on.

"Analogues" encompass functional and non-functional polypeptides which have at least about 40% amino acid sequence identity to human heparanase notwithstanding to occurrence of any non-naturally occurring amino acid analogues therein.

The term "derivative" in relation to endoglucuronidase or heparanase polypeptide described herein shall be taken to refer hereinafter to mutants, parts or fragments derived from the heparanase polypeptide which may or may not possess the activity of the functional protein. Derivatives include modified peptides in which ligands are attached to one or more of the amino acid residues contained therein, such as carbohydrates, enzymes, proteins, polypeptides or reporter molecules such as radionuclides or fluorescent compounds. Glycosylated, fluorescent, acylated or alkylated forms of the subject peptides are particularly contemplated by the present invention. Additionally, derivatives of heparanase which comprise fragments or parts of an amino acid sequence disclosed herein are within the scope of the invention, as are homopolymers or heteropolymers comprising two or more copies of the subject polypeptides. Procedures for derivatizing peptides are well-known in the art.

Substitutions encompass amino acid alterations in which an amino acid of the base polypeptide (i.e. heparanase) is replaced with a different naturally-occurring or a non-conventional amino acid residue. Such substitutions may be classified as "conservative", in which case an amino acid residue contained in the base polypeptide is replaced with another naturally-occurring amino acid of similar character, for example Gly↔Ala, Val↔Ile↔Leu, Asp↔Glu, Lys↔Arg, Asn↔Gln or Phe↔Trp↔Tyr.

Substitutions encompassed by the present invention may also be "non-conservative", in which an amino acid residue which is present in the base polypeptide is substituted with an amino acid having different properties, such as a naturally-occurring amino acid from a different group (eg. substituted a charged or hydrophobic amino acid with alanine), or alternatively, in which a naturally-occurring amino acid is substituted with a non-conventional amino acid.

Amino acid substitutions are typically of single residues, but may be of multiple residues, either clustered or dispersed.

Naturally-occurring amino acids include those listed in Table 1. Non-conventional amino acids encompassed by the invention include, but are not limited to those listed in Table 2.

Amino acid deletions will usually be of the order of about 1–10 amino acid residues, while insertions may be of any length. Deletions and insertions may be made to the N-terminus, the C-terminus or be internal deletions or insertions. Generally, insertions within the amino acid sequence will be smaller than amino-or carboxyl-terminal fusions and of the order of 1–4 amino acid residues.

Those skilled in the art will be aware that several means for producing homologue, analogue or derivatives of a base polypeptide are possible when provided with the isolated nucleic acid molecule which encodes said polypeptide, for example site-directed mutagenesis of DNA and polymerase chain reaction utilising mutagenised oligonucleotide primers, amongst others.

Accordingly, the present invention clearly extends to any and all homologue, analogue or derivatives of the endoglucuronidase or heparanase polypeptides of the present invention.

TABLE 1

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methyl butyrate | Mgabu | L-N-methylarginine | Nmarg |
| | | L-N-methylasparagine | Nmasn |
| aminocyclopropane-carboxylate | Cpro | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
| | | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-amino-butyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | | |
| D-α-methylcysteine | Dmcys | α-methylpenicillanine | Mpen |
| D-α-methylglutamine | Dmgln | N-(4-aminobutyl)glycine | Nglu |
| D-α-methylhistidine | Dmhis | | |
| D-α-methylisoleucine | Dmile | | |
| D-α-methylleucine | Dmleu | | |
| D-α-methyllysine | Dmlys | | |
| D-α-methylmethionine | Dmmet | | |
| D-α-methylornithine | Dmorn | | |
| D-α-methylphenylalanine | Dmphe | | |
| D-α-methylproline | Dmpro | | |

TABLE 2-continued

| Non-conventional amino acid | Code | Non-conventional amino acid | Code |
|---|---|---|---|
| D-α-methylserine | Dmser | N-(2-aminoethyl)glycine | Naeg |
| D-α-methylthreonine | Dmthr | | |
| D-α-methyltryptophan | Dmtrp | N-(3-aminopropyl)glycine | Norn |
| D-α-methyltyrosine | Dmty | | |
| D-α-methylvaline | Dmval | N-amino-α-methyl-butyrate | Nmaabu |
| D-N-methylalanine | Dnmala | | |
| D-N-methylarginine | Dnmarg | α-napthylalanine | Anap |
| D-N-methylasparagine | Dnmasn | N-benzylglycine | Nphe |
| D-N-methylaspartate | Dnmasp | N-(2-carbamylethyl)glycine | Ngln |
| D-N-methylcysteine | Dnmcys | | |
| D-N-methylglutamine | Dnmgln | N-(carbamylmethyl)glycine | Nasn |
| D-N-methylglutamate | Dnmglu | | |
| D-N-methylhistidine | Dnmhis | N-(2-carboxyethyl)glycine | Nglu |
| D-N-methylisoleucine | Dnmile | | |
| D-N-methylleucine | Dnmleu | N-(carboxymethyl)glycine | Nasp |
| D-N-methyllysine | Dnmlys | | |
| N-methylcyclohexylalanine | Nmchexa | N-cyclobutylglycine | Ncbut |
| | | N-cycloheptylglycine | Nchep |
| D-N-methylornithine | Dnmorn | N-cyclohexylglycine | Nchex |
| N-methylglycine | Nala | N-cyclodecylglycine | Ncdec |
| N-methylaminoisobutyrate | Nmaib | N-cylcododecylglycine | Ncdod |
| N-(1-methylpropyl)glycine | Nile | N-cyclooctylglycine | Ncoct |
| | | N-cyclopropylglycine | Ncpro |
| N-(2-methylpropyl)glycine | Nleu | N-cycloundecylglycine | Ncund |
| | | N-(2,2-diphenylethyl)glycine | Nbhm |
| D-N-methyltryptophan | Dnmtrp | | |
| D-N-methyltyrosine | Dnmtyr | N-(3,3-diphenylpropyl)glycine | Nbhe |
| D-N-methylvaline | Dnmval | | |
| γ-aminobutyric acid | Gabu | N-(3-guanidinopropyl)glycine | Narg |
| L-t-butylglycine | Tbug | | |
| L-ethylglycine | Etg | N-(1-hydroxyethyl)glycine | Nthr |
| L-homophenylalanine | Hphe | | |
| L-α-methylarginine | Marg | N-(hydroxyethyl))glycine | Nser |
| L-α-methylaspartate | Masp | | |
| L-α-methylcysteine | Mcys | N-(imidazolylethyl))glycine | Nhis |
| L-α-methylglutamine | Mgln | | |
| L-α-methylhistidine | Mhis | N-(3-indolylethyl)glycine | Nhtrp |
| L-α-methylisoleucine | Mile | | |
| L-α-methylleucine | Mleu | N-methyl-γ-amino-butyrate | Nmgabu |
| L-α-methylmethionine | Mmet | | |
| L-α-methylnorvaline | Mnva | D-N-methylmethionine | Dnmmet |
| L-α-methylphenylalanine | Mphe | N-methylcyclopentylalanine | Nmcpen |
| L-α-methylserine | Mser | | |
| L-α-methyltryptophan | Mtrp | D-N-methylphenylalanine | Dmnphe |
| L-α-methylvaline | Mval | | |
| N-(N-(2,2-diphenylethyl)carbamylmethyl)glycine | Nnbhm | D-N-methylproline | Dnmpro |
| | | D-N-methylserine | Dnmser |
| 1-carboxy-1-(2,2-diphenyl-ethylamino)cyclopropane | Nmbc | D-N-methylthreonine | Dnmthr |
| | | N-(1-methylethyl)glycine | Nval |
| | | N-methyla-napthylalanine | Nmanap |
| | | N-methylpenicillamine | Nmpen |
| | | N-(p-hydroxyphenyl)glycine | Nhtyr |
| | | N-(thiomethyl)glycine | Ncys |
| | | penicillamine | Pen |
| | | L-α-methylalanine | Mala |
| | | L-α-methylasparagine | Masn |
| | | L-α-methyl-t-butylglycine | Mtbug |
| | | L-methylethylglycine | Metg |
| | | L-α-methylglutamate | Mglu |
| | | L-α-methylhomophenylalanine | Mhphe |
| | | N-(2-methylthioethyl)glycine | Nmet |
| | | L-α-methyllysine | Mlys |
| | | L-α-methylnorleucine | Mnle |
| | | L-α-methylornithine | Morn |
| | | L-α-methylproline | Mpro |
| | | L-α-methylthreonine | Mthr |
| | | L-α-methyltyrosine | Mtyr |
| | | L-N-methylhomophenylalanine | Nmhphe |

TABLE 2-continued

| Non-conventional amino acid | Code | Non-conventional amino acid | Code |
| --- | --- | --- | --- |
| | | N-(N-(3,3-diphenyl-propyl)carbamyl-methyl)glycine | Nnbbe |

The isolated nucleic acid molecule of the invention is preferably derived from a mammalian source, such as a human or laboratory animal such as, a mouse, rabbit or rat, amongst others. In a particularly preferred embodiment, the isolated nucleic acid molecule is derived from a human.

As used herein, the term "derived from" shall be taken to refer to the origin of an integer or group of integers from a specified source, but not to the exclusion of other possible source or sources of said integers or group of integers.

The invention clearly extends to all tissue sources of the subject nucleic acid molecule, in particular wherein the isolated nucleic acid molecule comprises genomic DNA.

Preferred tissue sources of mRNA encoding an endoglucuronidase polypeptide or heparanase polypeptide include liver, placenta, spleen, platelets, macrophages and tumour cells such as, but not limited to melanoma cells, mammary adenocarcinoma cells, colonic carcinoma cells and B16 tumour cells, amongst others.

In a particularly preferred embodiment of the invention, the isolated nucleic acid molecule is derived from human platelets, murine spleen T-cells or rat MAT cells.

A further aspect of the present invention contemplates a nucleic acid molecule which encodes or is complementary to a nucleic acid molecule which encodes, an endoglucuronidase polypeptide wherein said nucleic acid molecule is capable of hybridising under at least low stringency conditions to the nucleic acid molecule set forth in any one of <400>12 or <400>14 or <400>16 or <400>18 or a complementary strand thereto.

For the purposes of nomenclature, the nucleotide sequence set forth in <400>12 relates to the cDNA encoding human platelet heparanase, and endoglucuronidase enzyme encompassed by the present invention. The nucleotide sequence set forth in <400>14 relates to a variant cDNA encoding human platelet heparanase. The nucleotide sequence set forth in <400>16 relates to the mouse activated spleen T cell-derived partial heparanase cDNA fragment produced by PCR using the oligonucleotides designated BamHepN and mhep3. The nucleotide sequence set forth in <400>18 relates to the rat MAT cell-derived partial heparanase cDNA fragment produced by PCR using the oligonucleotides designated BamHepN and dT-Not.

Those skilled in the art will be aware that variants of the human platelet heparanase cDNA sequence set forth in any one of <400>12 or <400>14 or <400>16 or <400>18 may be isolated by hybridization under low stringency conditions. Such variants include any genomic sequences, cDNA sequences mRNA or other isolated nucleic acid molecules derived from humans or other mammals. Additional variants are not excluded.

Preferably, the nucleic acid molecule further comprises a nucleotide sequence which encodes, or is complementary to a nucleotide sequence which encodes, a heparanase polypeptide, more preferably a heparanase polypeptide having the catalytic activity described supra.

More preferably, the isolated nucleic acid molecule according to this aspect of the invention is capable of hybridising under at least medium stringency conditions to the nucleic acid molecule set forth in any one of <400>12 or <400>14 or <400>16 or <400>18 or to a complementary strand thereof.

Even more preferably, the isolated nucleic acid molecule according to this aspect of the invention is capable of hybridising under at least high stringency conditions to the nucleic acid molecule set forth in any one of <400>12 or <400>14 or <400>16 or <400>18 or to a complementary strand thereof.

For the purposes of defining the level of stringency, a low stringency is defined herein as being a hybridisation and/or a wash carried out in 6×SSC buffer, 0.1% (w/v) SDS at 28° C. Generally, the stringency is increased by reducing the concentration of SSC buffer, and/or increasing the concentration of SDS and/or increasing the temperature of the hybridisation and/or wash. A medium stringency comprises a hybridisation and/or a wash carried out in 0.2×SSC–2× SSC buffer, 0.1% (w/v) SDS at 42° C. to 65° C., while a high stringency comprises a hybridisation and/or a wash carried out in 0.1×SSC–0.2×SSC buffer, 0.1% (w/v) SDS at a temperature of at least 55° C. Conditions for hybridisations and washes are well understood by one normally skilled in the art. For the purposes of further clarification only, reference to the parameters affecting hybridisation between nucleic acid molecules is found in pages 2.10.8 to 2.10.16. of Ausubel et al. (1987), which is herein incorporated by reference.

In an even more preferred embodiment of the invention, the isolated nucleic acid molecule further comprises a sequence of nucleotides which is at least 40% identical to at least 10 contiguous nucleotides derived from any one of <400>12 or <400>14 or <400>16 or <400>18 or a complementary strand thereof.

Still more preferably, the isolated nucleic acid molecule further comprises a sequence of nucleotides which is at least 40% identical to at least 50 contiguous nucleotides derived from the sequence set forth in any one of <400>12 or <400>14 or <400>16 or <400>18 or a complementary strand thereof.

In determining whether or not two nucleotide sequences fall within these percentage limits, those skilled in the art will be aware that it is necessary to conduct a side-by-side comparison or multiple alignment of sequences. In such comparisons or alignments, differences may arise in the positioning of non-identical residues, depending upon the algorithm used to perform the alignment. In the present context, reference to a percentage identity between two or more nucleotide sequences shall be taken to refer to the number of identical residues between said sequences as determined using any standard algorithm known to those skilled in the art. For example, nucleotide sequences may be aligned and their identity calculated using the BESTFIT programme or other appropriate programme of the Computer Genetics Group, Inc., University Research Park, Madison, Wis., United States of America (Devereaux et al, 1984).

The present invention is particularly directed to a nucleic acid molecule which is capable of encoding a mammalian endoglucuronidase polypeptide, in particular mammalian heparanase polypeptide, for example human heparanase derived from platelets. The subject invention clearly contemplates additional genes to those specifically described herein which are derived from human platelets.

A genetic sequence which encodes or is complementary to a sequence which encodes a mammalian endoglucuronidase polypeptide such as human heparanase may correspond to the naturally occurring sequence or may differ by one or more nucleotide substitutions, deletions and/or additions. Accordingly, the present invention extends to any endoglucuronidase or heparanase genes and any functional genes, mutants, derivatives, parts, fragments, homologues or analogues thereof or non-functional molecules but which are at least useful as, for example, genetic probes, or primer sequences in the enzymatic or chemical synthesis of said gene, or in the generation of immunologically interactive recombinant molecules.

In a particularly preferred embodiment, the genetic sequences of the invention exemplified herein are employed to identify and isolate similar genes from other cells, tissues, or organ types of the same or a different species, or from the cells, tissues, or organs of another mammalian species, in particular a laboratory mammal such as a rat, mouse or rabbit.

According to this embodiment, genomic DNA, or mRNA or cDNA derived from said other cells, tissues or organs with a hybridisation effective amount of a first heparanase-encoding genetic sequence comprising any one of <400>12 or <400>14 or <400>16 or <400>18 or a complementary sequence, homologue, analogue or derivative thereof derived from at least 10 contiguous nucleotides of said first sequence, and then detecting said hybridisation.

For the present purpose, "homologues" of a nucleotide sequence shall be taken to refer to an isolated nucleic acid molecule which is substantially the same as the nucleic acid molecule of the present invention or its complementary nucleotide sequence, notwithstanding the occurrence within said sequence, of one or more nucleotide substitutions, insertions, deletions, or rearrangements.

"Analogues" of a nucleotide sequence set forth herein shall be taken to refer to an isolated nucleic acid molecule which is substantially the same as a nucleic acid molecule of the present invention or its complementary nucleotide sequence, notwithstanding the occurrence of any non-nucleotide constituents not normally present in said isolated nucleic acid molecule, for example carbohydrates, radiochemicals including radionucleotides, reporter molecules such as, but not limited to DIG, alkaline phosphatase or horseradish peroxidase, amongst others.

"Derivatives" of a nucleotide sequence set forth herein shall be taken to refer to any isolated nucleic acid molecule which contains significant sequence similarity to said sequence or a part thereof. Generally, the nucleotide sequence of the present invention may be subjected to mutagenesis to produce single or multiple nucleotide substitutions, deletions and/or insertions. Nucleotide insertional derivatives of the nucleotide sequence of the present invention include 5' and 3' terminal fusions as well as intra-sequence insertions of single or multiple nucleotides or nucleotide analogues. Insertional nucleotide sequence variants are those in which one or more nucleotides or nucleotide analogues are introduced into a predetermined site in the nucleotide sequence of said sequence, although random insertion is also possible with suitable screening of the resulting product being performed. Deletional variants are characterised by the removal of one or more nucleotides from the nucleotide sequence. Substitutional nucleotide variants are those in which at least one nucleotide in the sequence has been removed and a different nucleotide of nucleotide analogue inserted in its place.

In a particularly preferred embodiment, the heparanase-encoding genetic sequence is labelled with a reporter molecule capable of giving an identifiable signal (e.g. a radioisotope such as $^{32}P$ or $^{35}S$ or a biotinylated molecule).

Preferably, the first genetic sequence comprises at least 50 contiguous nucleotides, even more preferably at least 100 contiguous nucleotides and even more preferably at least 500 contiguous nucleotides, derived from any one of <400>12 or <400>14 or <400>16 or <400>18 or a complementary strand, homologue, analogue or derivative thereof.

The related genetic sequence thus identified may be in a recombinant form, in a virus particle, bacteriophage particle, yeast cell, animal cell, or a plant cell.

An alternative method contemplated in the present invention involves hybridising two nucleic acid "primer molecules" derived from the heparanase-encoding sequence exemplified herein, to a nucleic acid "template molecule" which at least comprises a nucleotide sequence encoding a related genetic sequence or a functional part thereof, wherein the first of said primers comprises contiguous nucleotides derived from any one of <400>12 or <400>14 or <400>16 or <400>18 or a homologue, analogue or derivative thereof and the second of said primers comprises contiguous nucleotides complementary to <400>12 or <400>14 or <400>16 or <400>18 or a homologue, analogue or derivative thereof, subject to the proviso that the first and second primers are not complementary to each other. Specific nucleic acid molecule copies of the template molecule are amplified enzymatically in a polymerase chain reaction, a technique that is well known to one skilled in the art.

In a preferred embodiment, each nucleic acid primer molecule is at least 10 nucleotides in length, more preferably at least 20 nucleotides in length, even more preferably at least 30 nucleotides in length, still more preferably at least 40 nucleotides in length and even still more preferably at least 50 nucleotides in length.

Furthermore, the nucleic acid primer molecules consists of a combination of any of the nucleotide adenine, cytidine, guanine, thymidine, or inosine, or functional analogues or derivatives thereof which are at least capable of being incorporated into a polynucleotide molecule without having an inhibitory effect on the hybridisation of said primer to the template molecule in the environment in which it is used.

Furthermore, one or both of the nucleic acid primer molecules may be contained in an aqueous mixture of other nucleic acid primer molecules, for example a mixture of degenerate primer sequences which vary from each other by one or more nucleotide substitutions or deletions. Alternatively, one or both of the nucleic acid primer molecules may be in a substantially pure form.

The nucleic acid template molecule may be in a recombinant form, in a virus particle, bacteriophage particle, yeast cell, animal cell, or a plant cell. Preferably, the nucleic acid template molecule is derived from a human or laboratory animal species.

Those skilled in the art will be aware that there are many known variations of the basic polymerase chain reaction procedure, which may be employed to isolate a related genetic sequence encoding an endoglucuronidase or heparanase polypeptide when provided with the nucleotide sequence set forth in any of <400>12 or <400>14 or <400>16 or <400>18. Such variations are discussed, for example, in McPherson et al (1991). The present invention extends to the use of all such variations in the isolation of related endoglucuronidase-encoding or heparanase-encoding genetic sequences using the nucleotide sequences exemplified herein.

The isolated nucleic acid molecule according to any one of the further embodiments may be cloned into a plasmid or bacteriophage molecule, for example to facilitate the preparation of primer molecules or hybridisation probes or for the production of recombinant gene products. Methods for the production of such recombinant plasmids, cosmids, bacteriophage molecules or other recombinant molecules are well-known to those of ordinary skill in the art and can be accomplished without undue experimentation. Accordingly, the invention further extends to any recombinant plasmid, bacteriophage, cosmid or other recombinant molecule comprising the nucleotide sequence set forth in any one of <400>12 or <400>14 or <400>16 or <400>18 or a complementary sequence, homologue, analogue or derivative thereof.

The nucleic acid molecule of the present invention is also useful for developing genetic constructs which express the endoglucuronidase polypeptide of the present invention, thereby providing for the production of the recombinant polypeptide in isolated cells or transformed tissues.

A third aspect of the present invention provides a genetic construct comprising an isolated nucleic acid molecule which encodes or is complementary to a nucleic acid molecule which encodes a mammalian endoglucuronidase polypeptide, in particular a mammalian heparanase polypeptide as described herein.

In a most preferred embodiment, the genetic construct is an expression vector.

The term "expression vector" refers to a genetic construct wherein an isolated nucleic acid molecule is provided in an expressible form by placing said molecule in operable connection with appropriate regulatory sequences such as promoters and terminators, which are required for cell-based expression to occur. In the present context, an expression vector includes genetic constructs in which an isolated nucleic acid molecule which encodes an endoglucuronidase or heparanase polypeptide is placed in operable connection with a suitable promoter in the sense orientation to facilitate expression of a recombinant polypeptide when the expression vector is introduced into a cell. An expression vector also encompasses genetic constructs in which the isolated nucleic acid molecule is placed in operable connection with a suitable promoter in the antisense orientation to facilitate the transcription of an inhibitory nucleic acid molecule, for example an antisense molecule, ribozyme or minizyme.

Accordingly, one embodiment of the invention provides an expression vector which is useful for the production of the recombinant endoglucuronidase or heparanase polypeptide or alternatively, an antisense molecule, ribozyme or minizyme, when introduced into a cell line or a virus particle and under conditions suitable for gene expression or at least transcription to occur. Such conditions will depend upon the selection of a suitable cell line and expression vector, including the selection of promoter and terminator sequences to regulate expression, and would be well-known to the person skilled in the art.

Reference herein to a "promoter" is to be taken in its broadest context and includes the transcriptional regulatory sequences of a classical genomic gene, including the TATA box which is required for the accurate transcription initiation in a eukaryotic cell, with or without a CCAAT box sequence or alternatively, the Pribnow box required for accurate expression in prokaryotic cells.

The promoter may include further regulatory elements (i.e. upstream activating sequences, enhancers and silencers) which alter gene expression in response to developmental and/or external stimuli, or in a tissue-specific manner. Preferred promoters may contain additional copies of one or more specific regulatory elements, to further enhance expression and/or to alter the spatial expression and/or temporal expression pattern. For example, regulatory elements which confer copper inducibility may be placed adjacent to a heterologous promoter sequence driving expression of a structural gene or recombinase gene, thereby conferring copper inducibility on the expression of said gene.

In the present context, the term "promoter" is also used to describe a synthetic or fusion molecule, or derivative which confers, activates or enhances expression in a cell.

A promoter is usually, but not necessarily, positioned upstream or 5', of a structural gene, the expression of which it regulates. Furthermore, the regulatory elements comprising a promoter are usually positioned within 2 kb of the start site of transcription of the gene.

Placing a gene or isolated nucleic acid molecule operably under the control of a promoter sequence means positioning said gene or isolated nucleic acid molecule such that its expression is controlled by the promoter sequence. Promoters are generally positioned 5' (upstream) to the genes that they control. In the construction of heterologous promoter/structural gene combinations it is generally preferred to position the promoter at a distance from the gene transcription start site that is approximately the same as the distance between that promoter and the gene it controls in its natural setting, i.e., the gene from which the promoter is derived. As is known in the art, some variation in this distance can be accommodated without loss of promoter function. Similarly, the preferred positioning of a regulatory sequence element with respect to a heterologous gene to be placed under its control is defined by the positioning of the element in its natural setting, i.e., the genes from which it is derived. Again, as is known in the art, some variation in this distance can also occur.

Those skilled in the art will recognise that the choice of promoter will depend upon the nature of the cell being transformed and when expression of the recombinase, structural gene or other gene contained in the genetic construct of the invention is required. Furthermore, it is well-known in the art that the promoter sequence used in the expression vector will also vary depending upon the level of expression required and whether expression is intended to be constitutive or regulated.

For expression in eukaryotic cells, the genetic construct generally comprises, in addition to the nucleic acid molecule of the invention, a promoter and optionally other regulatory sequences designed to facilitate expression of said nucleic acid molecule. The promoter may be derived form a genomic clone encoding a mammalian endoglucuronidase such as heparanase or alternatively, it may be a heterologous promoter derived from another genetic source. Promoter sequences suitable for expression of genes in eukaryotic cells are well-known in the art.

Suitable promoters for use in eukaryotic expression vectors include those capable of regulating expression in mammalian cells, insect cells such as Sf9 (*Spodoptera frugiperda*) cells, yeast cells and plant cells. Preferred promoters for expression in eukaryotic cells include the polyhedron promoter, the SV40 early promoter and the cytomegalovirus (CMV-IE) promoter, amongst others.

Wherein the expression vector is intended for the production of recombinant protein, the promoter is further selected such that it is capable of regulating expression in a cell which is capable of performing any post-translational modification to the polypeptide which may be required for the subject recombinant polypeptide to be functional, such as N-linked glycosylation. Cells suitable for such purposes may be readily determined by those skilled in the art. By way of exemplification, Chinese hamster ovary (CHO) cells may be employed to carry out the N-terminal glycosylation and signal sequence cleavage of a recombinant polypeptide produced therein. Alternatively, a baculovirus expression vector such as the pFastBac vector supplied by GibcoBRL may be used to express recombinant endoglucuronidase polypeptides in Sf9 (*Spodoptera frugiperda*) cells, following standard protocols.

Figure 2:
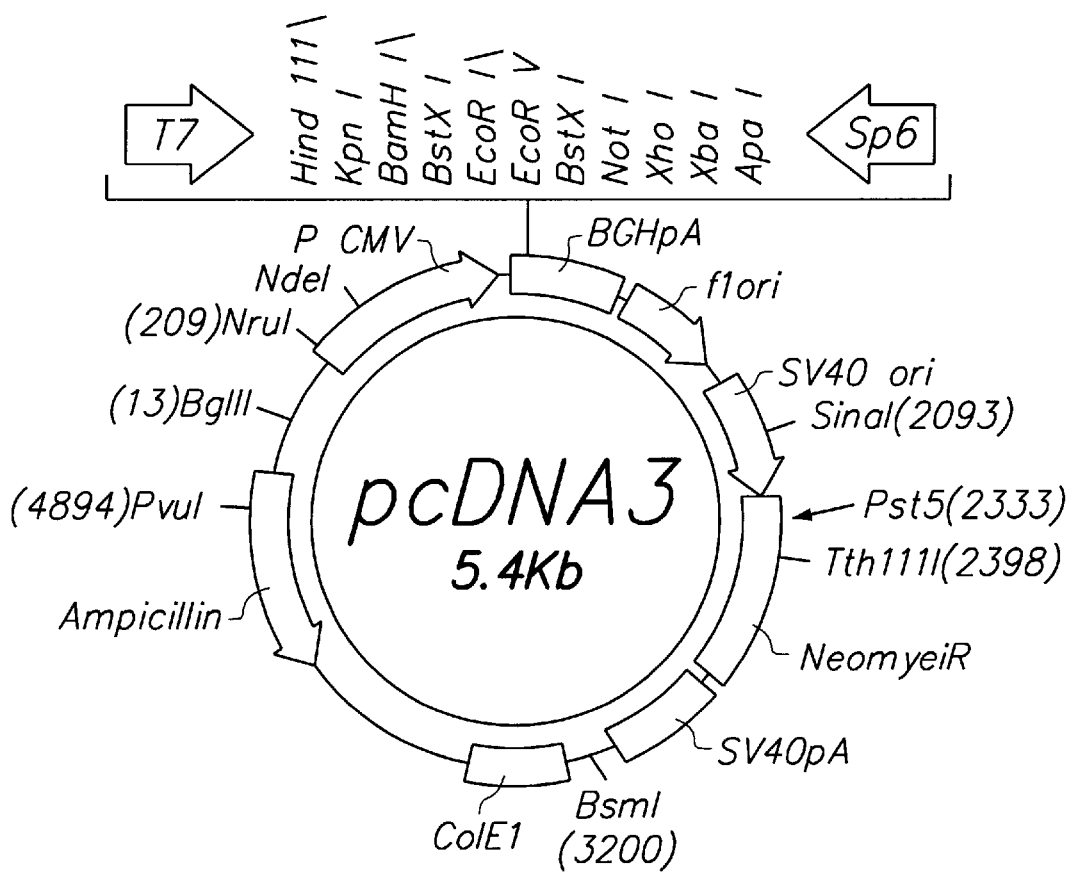
FIG. 2 is a graphical representation of the expression vector pcDNA3 (Invitrogen) showing the location of the cytomegalovirus IE promoter (P CMV), BGH terminator (BGH pA), SV40 origin of replication (SV40 ori), neomycin resistance gene (Neomycin), SV40 terminator (SV40 pA), bacterial origin of replication (ColE1) and ampicillin resistance gene (Ampicillin). The endoglucuronidase-coding sequences of the present invention are inserted in to the multiple cloning site (HindIII . . . ApaI) which is flanked by the T7 and SP6 promoter sequences.

Numerous expression vectors suitable for the present purpose have been described and are readily available. In a particularly preferred embodiment, the expression vector is based upon the pcDNA3 vector distributed by Medos Company Pty Ltd, Victoria, Australia which comprises the CMV promoter and BGH terminator sequences for regulating expression of the recombinant endoglucuronidase polypeptide of the invention in a eukaryotic cell, when isolated nucleic acid sequences encoding same are inserted, in the sense orientation relative to the CMF promoter, into the multiple cloning site of said vector. For the purposes of exemplification only, a map of the pcDNA3 vector is provided in FIG. 2.

Examples of eukaryotic cells contemplated herein to be suitable for expression include mammalian, yeast, insect, plant cells or cell lines such as COS, VERO, HeLa, mouse C127, Chinese hamster ovary (CHO), WI-38, baby hamster kidney (BHK), MDCK or Sf9 (insect) cell lines. Such cell lines are readily available to those skilled in the art.

The prerequisite for expression in prokaryotic cells such as *Escherichia coli* is the use of a strong promoter with an effective ribosome binding site. Typical promoters suitable for expression in bacterial cells such as *E. coli* include, but are not limited to, the lacz promoter, temperature-sensitive $\lambda_L$ or $\lambda_R$ promoters, T7 promoter or the IPTG-inducible tac promoter. A number of other vector systems for expressing the nucleic acid molecule of the invention in *E. coli* are well-known in the art and are described for example in Ausubel et al (1987).

Numerous vectors having suitable promoter sequences for expression in bacteria have been described, such as for example, pKC30 ($\lambda_L$:Shimatake and Rosenberg, 1981), pKK173-3 (tac: Amann and Brosius, 1985), pET-3 (T7: Studier and Moffat, 1986) or the pQE series of expression vectors (Qiagen, CA), amongst others.

Suitable prokaryotic cells include corynebacterium, salmonella, *Escherichia coli,* Bacillus sp. and Pseudomonas sp, amongst others. Bacterial strains which are suitable for the present purpose are well-known in the relevant art (Ausubel et al, 1987).

The term "terminator" refers to a DNA sequence at the end of a transcriptional unit which signals termination of transcription, in particular 3'-non-translated DNA sequences. In the case of terminators for transcription in prokaryotic cells, the terminator generally includes a polyadenylation signal, which facilitates the addition of polyadenylate sequences to the 3'-end of a primary transcript. They may be isolated from bacteria, fugi, viruses, animals and/or plants. Terminators active in eukaryotic and prokaryotic cells are known and described in the literature. Examples of terminators particularly suitable for use in the genetic constructs of the present invention include the BGH polyadenylation sequence.

The genetic constructs described herein may further comprise genetic sequences corresponding to a bacterial origin of replication and/or a selectable marker gene such as an antibiotic-resistance gene, suitable for the maintenance and replication of said genetic construct in a prokaryotic or eukaryotic cell, tissue or organism. Such sequences are well-known in the art.

Selectable marker genes include genes which when expressed are capable of conferring resistance on a cell to a compound which would, absent expression of said selectable marker gene, prevent or slow cell proliferation or result in cell death. Preferred selectable marker genes contemplated herein include, but are not limited to antibiotic-resistance genes such as those conferring resistance to ampicillin, Claforan, gentamycin, G-418, hygromycin, rifampicin, kanamycin, neomycin, spectinomycin, tetracycline or a derivative or related compound thereof or any other compound which may be toxic to a cell.

The origin of replication or a selectable marker gene will be spatially-separated from those genetic sequences which encode the recombinant endoglucuronidase or heparanase polypeptide.

In one particularly preferred embodiment of the present invention, the expression vector is intended for production of a recombinant mammalian endoglucuronidase or heparanase polypeptide. Accordingly, in such embodiments, it is essential that the nucleotide sequence which encodes which polypeptide be placed in the sense orientation relative to the promoter sequence to which it is operably connected.

Preferably, the recombinant polypeptide which is produced is functional. Those skilled in the art will realise that notwithstanding that the nucleic acid molecule of the invention is derived from a mammalian cell, it may be possible to express a functional recombinant polypeptide encoded thereof in either a prokaryotic or eukaryotic cell line. Appropriate cell lines for expression of a functional recombinant endoglucuronidase polypeptide may readily be determined without undue experimentation. Preferably however, the recombinant polypeptide is expressed using a eukaryotic cell line, more preferably a mammalian cell line such as any one of the cell lines described supra.

Preferably, the recombinant polypeptide produced comprises an amino acid sequence which is at least 40% identical to any one or more of <400>1–11 or <400>13 or <400>15 or <400>17 or <400>19 or <400>23 or a homologue, analogue or derivative thereof, more preferably including any post-translational modification thereto, in particular one or more glycosylated amino acids.

In an alternative embodiment, the recombinant endoglucuronidase or heparanase polypeptide is produced as an "in-frame" fusion polypeptide with a second polypeptide, for example a detectable reporter polypeptide such as β-galactosidase, β-glucuronidase, luciferase or other enzyme or a hapten peptide such as a poly-lysine or poly-histidine or other polypeptide molecule.

By "in-frame" means that a nucleotide sequence which encodes a first polypeptide is placed (i.e. cloned or ligated) in the same open reading frame adjacent to a nucleotide sequence which encodes a second polypeptide with no intervening stop codons there between, such that when the ligated nucleic acid molecule is expressed, a single fusion polypeptide is produced which comprises a sequence of amino acids corresponding to the summation of the individual amino acid sequences of the first and second polypeptides.

In order to produce a fusion polypeptide, the nucleic acid molecule which encodes the endoglucuronidase or heparanase polypeptide or a homologue, analogue or derivative thereof is cloned adjacent to a second nucleic acid molecule encoding the second polypeptide, optionally separated by a spacer nucleic acid molecule which encodes one or more amino acids (eg: poly-lysine or poly histidine, amongst others), such that the first coding region and the second coding region are in the same open reading frame, with no intervening stop codons between the two coding regions. When translated, the polypeptide thus produced comprises a fusion between the polypeptide products of the first and second coding regions. Wherein a spacer nucleic acid molecule is utilised in the genetic construct, it may be desirable for said spacer to at least encode an amino acid sequence which is cleavable to assist in separation of the fused polypeptide products of the first and second coding regions, for example a thrombin cleavage site.

A genetic construct which encodes a fusion polypeptide further comprises at least one start codon and one stop codon, capable of being recognised by the cell's translational machinery in which expression is intended.

Preferably, a genetic construct which encodes a fusion polypeptide may be further modified to include a genetic sequence which encodes a targeting signal placed in-frame with the coding region of the endoglucuronidase-encoding or heparanase-encoding nucleotide sequence, to target the expressed recombinant endoglucuronidase polypeptide or heparanase polypeptide to the extracellular matrix. More preferably, the genetic sequence encoding targeting signal is placed in-frame at the 5'-terminus or the 3'-terminus, but most preferably at the 5'-terminus, of the coding region of the nucleotide sequence which encodes the endoglucuronidase or heparanase polypeptide.

Methods for the production of a fusion polypeptide are well-known to those skilled in the art.

In order to produce the recombinant endoglucuronidase or heparanase polypeptide of the invention, the expression vector described herein is introduced into an appropriate cell line by any means known to those skilled in the art, for example by electroporation, calcium chloride transformation or PEG fusion, amongst others, to produce a transformed cell or transfected cell. The transformed or transfected cell is subsequently incubated for a time and under conditions sufficient for expression of the recombinant polypeptide encoded by the genetic construct to occur. Wherein the expression vector further includes a selectable marker gene, the transformed or transfected cell line may be incubated on a media which at least comprises a compound against which the selectable marker gene confers resistance, thereby facilitating the selection of cells which contain the expression vector and express the selectable marker gene at least.

The recombinant polypeptide thus produced may be partially-purified or purified to substantial homogeneity from the cell in which it is produced, using the method described by the present invention for the purification of platelet heparanase (Example 1) or a modification thereof.

Alternatively, wherein the recombinant polypeptide is expressed as a fusion polypeptide, it is also possible to purify the fusion polypeptide based upon its properties (eg size, solubility, charge etc). Alternatively, the fusion polypeptide may be purified based upon the properties of the non-endoglucuronidase moiety of said fusion polypeptide, for example substrate affinity. Once purified, the fusion polypeptide may be cleaved to release the intact endoglucuronidase polypeptide of the invention.

The isolated or purified recombinant endoglucuronidase polypeptide, in particular recombinant heparanase, is useful for any application wherein it is desirable to inhibit neovascularisation and its associated processes in the regulation of tissue development, inflammation, wound healing and/or tumour metastasis.

Additionally, the isolated or purified recombinant endoglucuronidase polypeptide, in particular recombinant heparanase, may be used to assist in the determination of the structure and/or sequence of sulphated molecules, particularly those sulphated molecules which at least comprise sulphated proteoglycans, sulphated oligosaccharides or heparan sulphate residues or side-chains, amongst others. By taking advantage of the functional nature of the recombinant polypeptide, a wide range of sulphated molecules may be subjected to digestion in the presence of the recombinant polypeptide of the invention for a time and under conditions sufficient to cleave the sulphated oligosaccharide moiety therefrom which may, if necessary, be subjected to ultra-structure determination using mass spectrometry, infrared spectroscopy, nuclear magnetic resonance (NMR) spectroscopy or ultraviolet spectroscopy, amongst another methods known to those skilled in the art.

Additionally, recombinant endoglucuronidase polypeptide, in particular recombinant heparanase, may be used in the preparation of immunologically interactive molecules, such as antibodies or functional derivatives thereof including Fabs or SCABS (single-chain antibodies), antibodies conjugated to an enzyme, radioactive or fluorescent tag. The present invention extends to a recombinant and synthetic antibodies and to antibody hybrids. A "synthetic antibody" is considered herein to include fragments and hybrids of antibodies.

Both polyclonal and monoclonal antibodies are obtainable by immunisation with an appropriate recombinant polypeptide or an epitope thereof or a peptide fragment thereof, using procedures well-known to those skilled in the art.

Accordingly, the present invention clearly extends to immunologically-interactive molecules which are capable of binding to a mammalian recombinant endoglucuronidase or heparanase polypeptide.

Most preferably, the immunologically interactive molecule is an antibody molecule. The antibody molecule may be monooclonal or polyclonal and may be used for developing enzyme-linked immunosorbent assays (ELISA) or other immunoassays for the rapid diagnosis of elevated heparanase expression in human or animal cells and tissues to assist in the diagnosis of conditions associated therewith, such as angiogenesis, angioplasty-induced restenosis, atherosclerotic plaque formation and inflammation, amongst others. The invention described herein extends to all such uses of immunointeractive molecules and diagnostic assays which require said immunoassays for their performance.

A wide range of immunoassay techniques may be such as those described in U.S. Pat. Nos. 4,016,043, 4,424,279 and 4,018,653. By way of example only, an antibody raised against recombinant platelet heparanase is immunobilised onto a solid substrate and a biological sample from an animal to be tested for the presence of elevated heparanase expression, for example serum or isolated platelets, is brought into contact with the bound molecule. After a suitable period of incubation, for a period of time sufficient to allow formation of an antibody-antigen complex, a second antibody labelled with a reporter molecule capable of producing a detectable signal is then added and incubated, allowing sufficient time for the formation of a tertiary complex of antibody-antigen-labelled antibody. Any unreacted material is washed away, and the presence of the tertiary complex is determined by observation of a signal produced by the reporter molecule. The results may either be qualitative, by simple observation of the visible signal or may be quantiated by comparison with a control sample containing known amounts of heparanase. Variations of this assay include a simultaneous assay, in which both sample and labelled antibody are added simultaneously to the bound antibody, or a reverse assay in which the labelled antibody and sample to be tested are first combined, incubated and then added simultaneously to the bound antibody. These techniques are well known to those skilled in the art, and the possibility of minor variations will be readily apparent.

The solid substrate is typically glass or a polymer, the most commonly used polymers being cellulose, polyacrylamide, nylon, polystyrene, polyvinyl chloride or polypropylene. The solid supports may be in the form of tubes, beads, discs or microplates, or any other surface suitable for conducting an immunoassay. The binding processes are well-known in the art and generally consist of cross-linking covalently binding or physically adsorbing the molecule to the insoluble carrier.

By "reporter molecule", as used in the present specification, is meant a molecule which, by its chemical nature, produces an analytically identifiable signal which allows the detection of antigen-bound antibody. Detection may be either qualitative or quantitative. The most commonly used reporter molecule in this type of assay are either enzymes, fluorophores or radionuclide containing molecules (i.e. radioisotopes). In the case of an enzyme immunoassay, an enzyme is conjugated to the second antibody, generally by means of glutaraldehyde or periodate. As will be readily recognised, however, a wide variety of different conjugation techniques exist which are readily available to one skilled in the art. Commonly used enzymes include horseradish peroxidase, glucose oxidase, β-galactosidase and alkaline phosphatase, amongst others. The substrates to be used with the specific enzymes are generally chosen for the production, upon hydrolysis by the corresponding enzyme, of a detectable colour change. It is also possible to employ fluorogenic substrates, which yield a fluorescent product.

Alternatively, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic colour visually detectable with a light microscope. As in the EIA, the fluorescent labelled antibody is allowed to bind to the first antibody-hapten complex. After washing off the unbound reagent, the remaining complex is then exposed to the light of the appropriate wavelength, the fluorescence observed indicates the presence of the hapten of interest. Immunofluoroescence and EIA techniques are both very well established in the art and are particularly preferred for the present method. However, other reporter molecules, such as radioisotope, chemiluminescent or bioluminescent molecules, may also be employed. It will be readily apparent to the skilled technician how to vary the procedure to suit the required purpose.

The immunologically-interactive molecule is also useful in purifying the recombinant heparanase of the present invention. Methods for the affinity purification of proteins using antibodies are well-known to those skilled in the art.

In a further embodiment, the isolated nucleic acid molecule of the invention is placed in the antisense orientation relative to the promoter sequence to which it is operably connected such that when said nucleic acid molecule is expressed, an antisense molecule or ribozyme molecule is transcribed.

In the context of the present invention, an antisense molecule is an RNA molecule which is transcribed from the complementary strand of a nuclear gear to that which is normally transcribed to produce a "sense" mRNA molecule capable of being translated into a polypeptide. The antisense molecule is therefore complementary to the sense mRNA, or a part thereof. Although not limiting the mode of action of the antisense molecules of the present invention to any specific mechanism, the antisense RNA molecule possesses the capacity to form a double-stranded mRNA by base pairing with the sense mRNA, which may prevent translation of the sense mRNA and subsequent synthesis of a polypeptide gene product.

Ribozymes are synthetic RNA molecules which comprise a hybridising region complementary to two regions, each of at least 5 contiguous nucleotide bases in the target sense mRNA. In addition, ribozymes possess highly specific endoribonuclease activity, which autocatalytically cleaves the target sense mRNA. A complete description of the function of ribozymes is presented by Haseloff and Gerlach (1988) and contained in International Patent Application No. WO89/05852. The present invention extends to ribozymes which target a sense mRNA encoding a mammalian endoglucuronidase polypeptide described herein, in particular human heparanase, thereby hybridising to said sense mRNA and cleaving it, such that it is not longer capable of being translated to synthesise a functional polypeptide product.

According to this embodiment, the present invention provides a ribozyme or antisense molecule comprising a sequence of contiguous nucleotide bases which are able to form a hydrogen-bonded complex with a part of the endoglucuronidase or heparanase mRNA at least about 10 to 20 contiguous nucleotides derived from any one of <400>12 or <400>14 or <400>16 or <400>18 or a complementary sequence thereto, preferably at least about 20–50 contiguous nucleotides derived from any one of <400>12 or <400>14 or <400>16 or <400>18 or a complementary sequence thereto, or still more preferably at least about 50–500 contiguous nucleotides derived from any one of <400>12 or <400>14 or <400>16 or <400>18 or a complementary sequence thereto, or still more preferably to the full-length or substantially full-length endoglucuronidase or heparanase mRNA sequence.

It is understood in the art that certain modifications, including nucleotide substitutions amongst others, may be made to the antisense and/or ribozyme molecules of the present invention, without destroying the efficacy of said molecules in inhibiting the expression of an endoglucuronidase gene, in particular a human heparanase gene. It is therefore within the scope of the present invention to include any nucleotide sequence variants, homologues, analogues, or fragments of the said gene encoding same, the only requirement being that said nucleotide sequence variant, when transcribed, produces an antisense and/or ribozyme molecule which is capable of hybridising to the said sense mRNA molecule.

The ribozyme and antisense molecules of the invention are particularly useful in the prophylactic and therapeutic treatment of conditions associated with the elevated expression of heparanase in human or animal cells, such as metastasis, angiogenesis, angioplasty-induced restenosis, atherosclerotic plaque formation and inflammation, amongst others. According to this embodiment, the subject antisense or ribozyme molecule or a genetic construct expressing same may be administered to a human or animal subject for a time and under conditions sufficient to reduce or prevent the expression of the endogenous heparanase enzyme at an inflammation site, tumour site, in the extracellular matrix or endothelial surface, amongst others.

In the case of "naked" antisense or ribozyme molecules administered directly to the subject, those skilled in the art are aware that it may be necessary to include modified nucleotide residues, nucleotide analogues or other substituents to reduce or inhibit or prevent degradation of said molecules by cellular nuclease enzymes, thereby increasing their half-life following administration. Such modified nucleic acid molecules are well-known to those skilled in the art.

In the case of genetic constructs which express the subject antisense or ribozyme molecules described herein, those skilled in the art will be aware that it will be important for the antisense or ribozyme molecule to be expressed following its administration to the subject, in order to achieve the advantageous effects of the invention in reducing heparanase expression.

Still yet another aspect of the invention contemplates a method of identifying a modulator of heparanase activity, said method comprising assaying recombinant heparanase activity in the presence of a potential modulator and comparing said activity to the activity of recombinant heparanase in the absence of said potential modulator.

As used herein, the term "modulator" shall be taken to refer to any chemical compound, molecule or macromolecule which is capable of altering the enzyme activity of an endoglucuronidase polypeptide, in particular a heparanase polypeptide, including both agonists and antagonists of said enzyme activity.

Preferably, the subject method further comprises the first step of expressing a functional recombinant endoglucuronidase polypeptide or heparanase polypeptide in a cell for a time and under conditions sufficient for said polypeptide to be produced in an assayable quantity.

The term "assayable quantity" refers to a level of expression of a recombinant polypeptide which is sufficient for the activity of said polypeptide to be determined by any standard enzyme assay procedure which is specific for the enzymic function of the recombinant polypeptide.

In a particularly preferred embodiment of the invention, the modulator is an antagonist molecule. According to this embodiment, the recombinant heparanase activity detected in the presence of said modulator is significantly less than that detected in the absence of said modulator, under substantially similar reaction conditions.

Preferred modulators of an endoglucuronidase or heparanase enzyme activity are capable of inhibiting or reducing said enzyme activity as measured in vitro or in vivo by at least about 20%, more preferably by at least about 50% and even more preferably by at least about 80%, compared to the enzyme activity which is detectable in the absence of said modulator.

In an alternative embodiment, the modulator of an endoglucuronidase or heparanase enzyme activity is capable of inhibiting or reducing said enzyme activity to a level sufficient to significantly reduce the level of neovascularisation and/or the proliferation of smooth muscle cells or alternatively, to reduce the level of degradation of endothelial cell surface HSPG and/or extracellular matrix HSPG by at least about 20%, more preferably by at least about 50% and even more preferably by at least about 80%.

A further aspect of the invention contemplates an inhibitor of a mammalian endoglucuronidase polypeptide enzyme activity, in particular a mammalian heparanase.

As used herein, the term "inhibitor" refers to any modulator of enzyme activity as hereinbefore defined or a nucleic acid molecule, such as a nucleic acid molecule which is capable of reducing the level of expression of a mammalian endoglucuronidase polypeptide, in particular a heparanase polypeptide in a cell, tissue or organ, wherein the reduced expression leads to a reduction in the level of assayable endoglucuronidase or heparanase enzyme activity.

The inhibitor molecule of the present invention may be a non-cleavable substrate of a heparanase polypeptide or a negatively-charged molecule such as sulphated oligosaccharide, sulphonate, phosphate or phosphonate, amongst others, or alternatively an antibody molecule or catalytic antibody molecule capable of binding and inhibiting the activity of a heparanase polypeptide or alternatively, a nucleic acid inhibitor molecule sucha s ribozyme, minizyme or antisense molecule, amongst others which is capable of inhibiting the expression of a heparanase polypeptide in a cell at the nucleic acid level, the only requirement being that said inhibitor molecule is at least capable of reducing the activity of a heparanase polypeptide at a wound site, tumour cell, extracellular matrix or endothelial surface, amongst others.

In a particularly preferred embodiment of the invention, the inhibitor molecule is a non-cleavable substrate or substrate analogue of a heparanase polypeptide, such as a sulphated oligosaccharide, sulphate or HSPG comprising same. More preferably, the inhibitor is one which is identified using the method described supra for the identification of modulators of endoglucuronidase enzyme activity.

The inhibitor molecules described herein is useful in a wide range of prophylactic and therapeutic applications, by virtue of their ability to inhibit heparanase enzymes. The inhibitor molecules encompassed by the invention are particularly useful as inhibitors of metastasis, angiogenesis, wound healing, angioplasty-induced restenosis, arteriosclerosis, atherosclerosis, inflammation or other physiological or medical condition wherein heparanase activity is elevated.

The advantageous effects of the invention are achieved by the administration of a pharmaceutical composition which at least comprises one or more of the inhibitory molecules described herein as an active ingredient, to a human or animal subject of injection, oral ingestion (e.g. in mediated food material) or topical administration.

The compositions may conveniently be presented in unit dosage from and may be prepared by any methods well known on the art. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. inert diluent, preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent.

Tablets or powders or granules may optionally be coated or scored and may be formulated so as to provide slow or controlled release of the active ingredient therein using, for example, hydroxypropylmethyl cellulose in varying proportions to provide the desired release profile. Additionally, sweeteners or dietary formulae may be included to improve their palatability to a specific animal subject. Optionally, such solid compositions be provided with an enteric coating, to provide release in parts of the gut other than the stomach.

The active compounds may also be administered in dispersions prepared in glycerol, liquid polyethylene glycols, and/or mixtures thereof and in oils. Under ordinary conditions of storage and use, these preparations contain a preservative to prevent the growth of microorganisms.

Pharmaceutical forms suitable for parenteral administration include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example.

Sterile injectable solutions are prepared by incorporating the active compounds in the required amount in the appropriate solvent with various of the other ingredients enumerated above, as required, followed by filter sterilisation. Generally, dispersions are prepared by incorporating the various sterilised active ingredient(s) into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The carriers, excipients and/or diluents utilised in the pharmaceutical compositions of the present invention should be acceptable for human or veterinary applications. Such carriers, excipients and/or diluents are well-known to those skilled in the art. Carriers and/or diluents suitable for veterinary use include any and all solvents, dispersion media, aqueous solutions, coatings, antibacterial and antifungal agents, isotonic and absorption delaying agents, and the like. Except insofar as any conventional media or agent is incompatible with the active ingredient, use thereof in the composition is contemplated. Supplementary active ingredients can also be incorporated into the compositions.

The compositions of this invention may include other agents conventional in the art. For example, compositions suitable for oral administration may include such further agents as dietary formulae, binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable time delay agents include glyceryl monostearate or glyceryl distearate.

The present invention is further described with reference to the following non-limiting Examples.

EXAMPLE 1

Purification and characterisation of mammalian heparanase

Human platelet heparanase was purified according to the method of Freeman and Parish International Patent Application No. PCT/AU97/00453]. Evidence of purity, as shown by SDS-PAGE, is depicted in FIG. 1. All samples were reduced with dithiothreitol prior to electrophoresis.

Purified human platelet heparanase had a Mr of 50 kDa as determined by SDS-PAGE analysis (FIG. 1) and by gel filtration. N-deglycosylation of the enzyme with recombinant N-glycosidase F obtained from Boehringer Mannheim (Sydney, Australia) resulted in a reduction in Mr to 40 kDa (FIG. 1). This is consistent with a Mr of 42 kDa as predicted from cDNA sequence for the de-glycosylated mature enzyme which encoded for 6 putative N-glycosylation sites (see Example 3). No further reduction in the apparent size of the N-deglycosylated material was observed following concurrent O-glycosidase and neuraminidase treatment (FIG. 1). The purified membrane bound enzyme also had a native Mr and subunit Mr of 50 kDa as determined by gel filtration and SDS-PAGE analysis under reducing conditions (FIG. 1).

EXAMPLE 2

N-terminal and tryptic digest sequence determination

Using the method of Hellman et al. (1995), in situ trypsin digestion of the 50 kDa band obtained following SDS-PAGE analysis of purified human platelet heparanase resulted in the isolation of 11 peptides which were amino acid sequenced using a Perkin Elmer Applied Biosystems Procise 494 protein sequencer. The 50 kDa band was excised, passively transferred to PVDF nylon membrane, and the N-terminal sequence obtained by the method of Messer et al. (1997).

The amino acid sequences of the trypsin digest-generated peptides and the N-terminal sequence are shown in Table 3 (i.e. <400>1–11 corresponding to peptides 1–11, respectively of Table 3).

Comparison of the peptides and the N-terminal sequence with the amino acid sequence data base demonstrated no highly significant or consistent homologies with any known proteins. Peptides 2 and 3 were identical except peptide 2 was one residue greater in length. Peptides 1 and 8 were identical except peptide 1 was two residues longer. Peptides 5 and 7 were minor sequences associated with peptides 4 and 6. The sequences were highly reliable for all the peptides with only a few residues being questionable. An interesting feature of peptide 10 was evidence for polymorphism at residues 2 and 3. This is not surprising as the platelet heparanse was prepared from pooled platelet preparations from many human donors.

EXAMPLE 3

Cloning of human heparanase cDNA

A cDNA clone designated as clone c1 (ATCC number 514661) was obtained from the American Tissue Type Collection, Maryland, USA. This cDNA clone was identified in a BLAST search of the EST database, for nucleotide sequences which might possible encode one or more of the amino acid sequences of human platelet heparanase obtained as described in the preceding example (<400>1–11). The c1 clone was shown by the present inventors to comprise nucleotide sequences capable of encoding at least four human platelet heparanase peptide sequences or sequences closely related thereto, in particular those sequences set forth in <400>1, 2, 9 and 10. These data strongly suggested that clone c1 encoded at least a part of the human platelet heparanase polypeptide.

Subsequent experiments by the inventors revealed that the c1 clone was approximately 1.1 kb in length, comprising nucleotides 774 to 1711 of <400>12, encoding the C-terminal end of heparanase.

The c1 clone was fully sequenced and utilized to design primers for PCR amplification of the 5' end of the mRNA. A fragment designated cλ, approximately 800 bp in length, was amplified from a λgt11 human placental cDNA library (ATCC number HL 1008). The cλ fragment was sequenced and shown to contain an overlapping 3' sequence with the partial cDNA clone, in particular nucleotides 1 to 816 of <400>12.

The cλ fragment was used to obtain two putative full length clones (designated c2 and c9), from the λgt11 human placental cDNA library, by hybridisation screening. Clone c9 encoded for the full length heparanase polypeptide, however it contained a 115 bp deletion from nucleotides 114 to 1258 of <400>12. Clone c2 comprised nucleotides 1 to 1481 of <400>12 and was thus truncated within 169 bp from the stop codon.

The full length cDNA and amino acid sequence of the heparanase enzyme was deduced (<400>12 and <400>13). The heparanase open reading frame set forth in <400>12 is 1629 nucleotides long and encodes for a 543 amino acid protein. The nucleotide sequence set forth in <400>12 contains a putative polyadenylation signal at positions 1679 to 1684.

Eight of the eleven isolated trypic digest peptides and the N-terminal sequence of the isolated enzyme was detected in the amino acid sequence encoded by the assembled full-length cDNA sequence (i.e. <400>1–3, <400>6, <400>8–11). Seven of these eight tryptic peptides were essentially identical to the amino acid sequence encoded by the cDNA sequence (i.e. <400>1–3 and <400>8–11). Peptide 6 was found as incomplete sequences in the cDNA sequence while peptides 4, 5 and 7 were not found. Whether these peptide sequences are derived from a protein impurity in the heparanase preparation, or represent differently spliced variations of the heparanase remains to be seen.

The mature isolated enzyme appears to be a truncated form with the N-terminus located 158 amino acid residues downstream from the putative initiation codon, because whilst the open reading frame extends from nucleotides 46 to 1674 of <400>12, the mature protein is encoded by nucleotides 517 to 1674 of <400>12. The predicted cDNA size encoding for the mature isolated protein (assuming there had been no C-terminus processing) is 42.2 kDa which is consistent with an apparent size of 40 kDa obtained when the human platelet enzyme was N-deglycosylated (FIG. 1).

The lysine acid residue at position 158 of the immature polypeptide set forth in <400>13 forms the N-terminus of the mature human heparanase polypeptide. Putative N-linked glycosylation sites exist at Asn162, Asn178, Asn200, Asn217, Asn238 and Asn459 in the immature full-length polypeptide.

EXAMPLE 4

Tissue distribution of human heparanase mRNA

The expression of human heparanase mRNA was analysed by Northern blot of various human tissues.

Northern analysis of multiple human tissue blots (Clonetech, Palo Alto, Calif.) was performed by probing membranes with the full length human heparanase cDNA, labelled by random priming (Megaprime DNA labelling system, Amersham), using Expresshyb solution (Clonetech) as specified by the manufacturers. Membranes were washed in 1×SSC for 40 minutes at room temperature followed by 0.1×SSC for 40 minutes at 60° C. and exposed to X-ray film.

Figure 3:
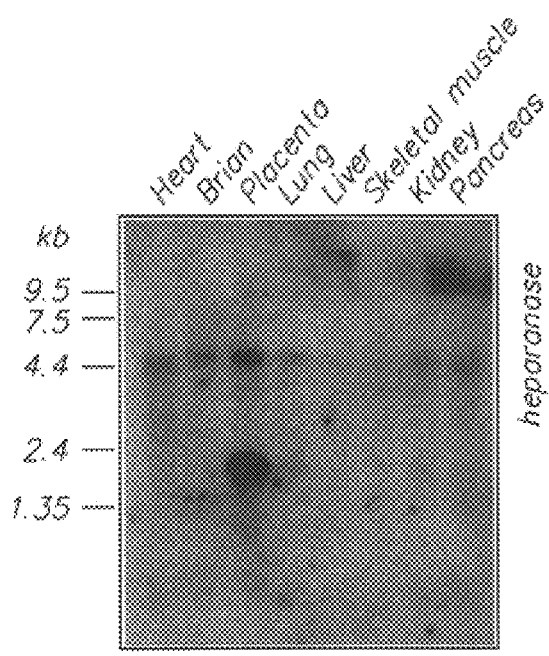
FIG. 3 is a copy of a photographic representation of a Northern blot hybridisation of mRNAs derived from non-immune heart, brain, placenta, lung, liver, skeletal muscle, kidney and pancreas tissues, following hybridisation with radioactively-labelled full-length human heparanase cDNA set forth in <400>12. Tissue sources are indicated at the top of each lane. Size markers (kb) are indicated at the left of the Figure.
Figure 4:
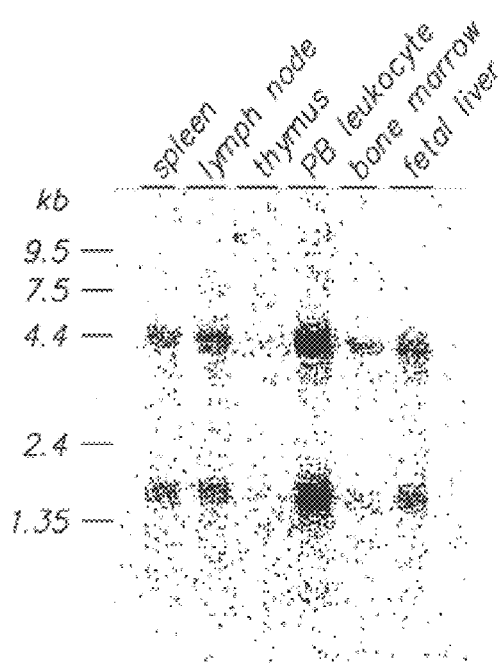
FIG. 4 is a copy of a photographic representation of a Northern blot hybridisation of mRNAs derived from immune spleen, lymph node, thymus, peripheral blood (PB) leukocyte, bone marrow and fetal liver tissues, following hybridisation with radioactively-labelled full-length human heparanase cDNA set forth in <400>12. Tissue sources are indicated at the top of each lane. Size markers (kb) are indicated at the left of the Figure.

In non-immune tissue, a message of the expected size based on the isolated heparanase cDNA clone (~2 kb), was detected in placenta but not in heart, brain, lung, liver, skeletal muscle, kidney or pancreas (FIG. 3). A second message of 4.4 kb was also detected in placenta but at a lower level than the 2 kb message. The 4.4 kb message was also detected weakly in all other tissues, and may represent an alternate splice varient or a product from a related gene (see blow). In immune tissues, both the 2 kb and 4.4 kb messages were detected in spleen, lymph node, thymus, peripheral blood leukocytes, bone marrow and fetal liver (FIG. 4). The highest levels of mRNA were seen in PBL, with lower levels in spleen, lymph node, bone marrow and fetal liver, and only weak expression in the thymus. The expression levels of the 2 kb and 4.4 kb messages appeared similar in each of the immune tissues, suggesting that both messages are derived from the same gene or from possibly from different genes that are coordinately regulated.

EXAMPLE 5

Southern blot analysis of the human heparanase gene

10 μg of human genomic DNA was restricted with a range of restriction enzymes and separated on a 1% agarose gel then transferred to a Hybond-N nylon filter Amersham, Arlington Heights, Ill.). The blot was probed with the full length human heparanase cDNA labelled by random priming and hybridised in a 50% formamide, 6×SSC, 0.5%SDS, 5×Denhardt's solution and 100 μg/ml salmon sperm DNA at 42° C. The membrane was washed in 1×SSC for 40 minutes at room temperature followed by 0.1×SSC for 40 minutes at 65° C. and exposed to X-ray film.

Figure 5:
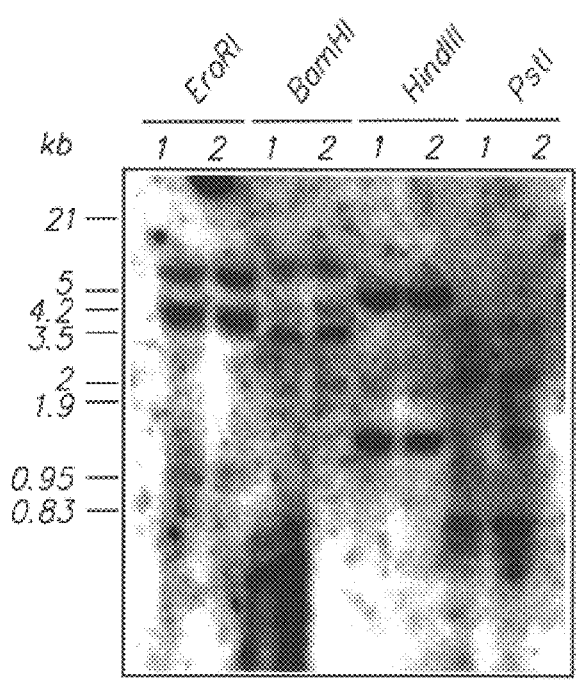
FIG. 5 is a copy of a photographic representation of a Genomic Southern blot hybridisation showing the gene organisation and copy number of the human heparanase gene. Genomic DNA from two individuals (lanes marked 1 and 2) was digested with the restriction enzymes EcoRI (lanes 1 and 2), BamHI (lanes 3 and 4), HindIII (lanes 5 and 6) or PstI (lanes 7 and 8), separated by electrophoresis on a 1% (w/v) agarose gel, transferred to nylon membrane and hybridised to a radioactively-labelled full-length human heparanase cDNA clone (<400>12). Enzymes used and source of DNA are indicated at the top of the lanes. Size markers (kb) are indicated at the left of the Figure. The arrow at the right-hand side of the Figure indicates the position of a polymorphic 1.4 kb PstI fragment that is present in individual 2 but not individual 1.

Southern analysis of human genomic DNA from two individuals digested with a range of restriction enzymes and probed with the full length human heparanase cDNA, revealed a simple hybridising band pattern, consistent with the human heparanase gene being a single copy gene (FIG. 5). Thus it is likely that the 4.4 kb message observed by Northern analysis is a splice varient rather than a product from a related gene.

EXAMPLE 6

Cloning of Mouse and Rat Heparanase cDNAs
(1) Isolation of RNA and first strand cDNA synthesis Total cellular RNA was prepared by homogenising 100 mg of tissue or $10^7$ cells in 1 ml of Trizol reagent (Gibco-BRL), upon which aqueous fraction was recovered and RNA precipitated using isopropanol. First strand cDNA was produced from 5 µg of total RNA by priming with an oligosaccharide dT primer (dT-Not, Table 2) using a First Strand cDNA synthesis system (Pharmacia Biotech) according to the manufacturers instructions.

(2) Polymerase chain reaction

Reactions were performed on 10 ng of first strand cDNAs in the presence of 100 ng of each oligonucleotide primer, 1.25 mM dNTPs, 50 mM KCl, 10 mM Tris-Cl pH 8.3 and 1.5 mM $MgCl_2$ using 1 unit of Taq DNA polymerase (Bresatec) for 40 amplification cycles.

(3) Nucleotide sequencing

PCR products or cDNA clones were sequenced by automated sequencing using an Applied Biosystems 377 sequencer.

(4) Cloning of cDNAs

PCR products were subcloned directly into the T-tailed vector pCR2.1 (Invitrogen) as described by the manufacturer.

(5) Identification of mouse heparanase using bioinformatics and cDNA cloning by PCR Mouse heparanase ESTs were identified by screening the dbest (public EST, GenBank) database with the human heparanase nucleic acid sequence using BLASTN (Table 4). The EST nucleotide sequences were retrieved using ENTREZ (NCBI) and contiguous sequences assembled from overlapping ESTs. The compiled EST sequences covered the 3' end of the mouse heparanase cDNA and corresponded to nucleotides 1004 to the polyadenylated tail of the human heparanase mRNA.

The nucleotide sequence of the mouse heparanase cDNA was extended by 513 bases towards the 5' end. This was achieved by performing PCR using the oligonucleotides BamHepN (corresponding to nucleotides 517–534 of the human heparanase cDNA) and mhep3 (corresponding to nucleotides 1234 to 1250 of the mouse heparanase cDNA (Table 5) on first stand cDNA made from total RNA isolated from activated 129 mouse spleen T cells.

The mouse heparanase cDNA fragment was sequenced directly and determined to be 1368 nucleotides in length (with nucleotides 1 to 513 being identical to that compiled from the ESTs) and to encode 386 amino acids of the C-terminal portion of the molecule (corresponding to amino acids 158–543 of human heparanase which comprises the predicted mature protein).

The nucleotide sequence and derived amino acid sequence of the murine heparanase cDNA are set forth in <400>16 and <400>17, respectively.

The predicted amino acid sequence contains 3 putative N-linked glycosylation sites at Asn37, Asn154 and Asn296 and a putative transmembrane region encompassed by residues 352–371. Alignment of the mouse and human heparanse amino acids sequences using PILEUP (NCBI)) indicated 80.8% identity (FIG. 5).

A clone of the mouse heparanse cDNA fragment (designated muhep-pCR2.1/1) was generated by subcloning the PCR fragment into the vector pCR2.1. The nucleotide sequence of this clone was identical to the sequence determined from the direct sequencing of the PCR product.

(6) Cloning of a rat heparanase cDNA clone by PCR

A rat heparanase cDNA fragment was generated by performing 3' Rapid Amplification of cDNA Ends (RACE)-PCR using the BamHepN oligonucleotide and a poly-dT primer (dT-Not) (Table 5) on first strand DNA derived from the rat MAT tumour cell line.

The nucleotide sequence and derived amino acid sequence of the rat heparanase cDNA are set forth in <400>18 and <400>19, respectively. The rat heparanase cDNA was sequenced directly and determined to be 1168 nucleotides in length and encode 386 amino acids of the C-terminal portion of the molecule (corresponding to amino acids 158–543 of human heparanase which comprises the mature protein).

Figure 6:
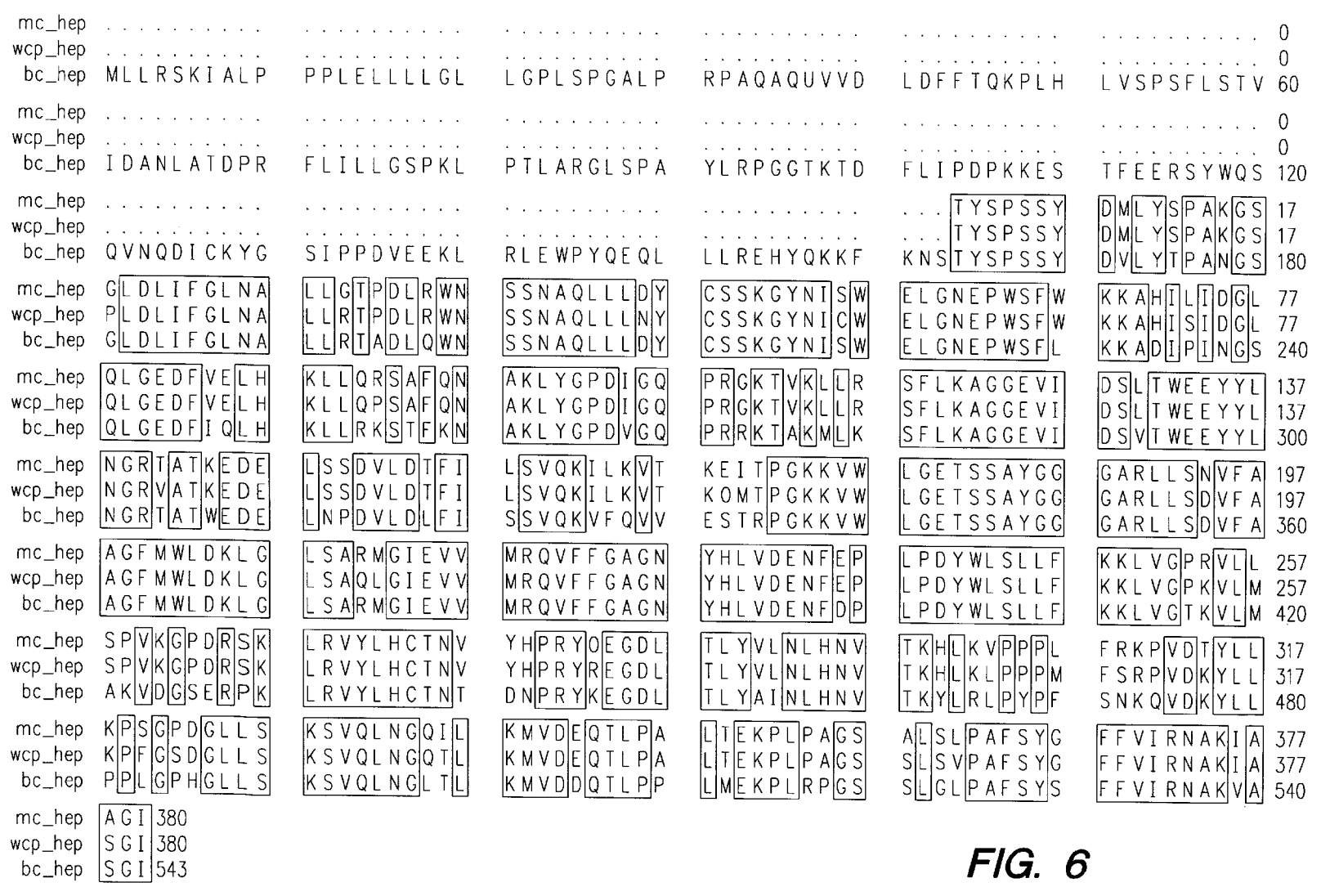

The predicted amino acid sequence contains 2 putative N-linked glycosylation sites at Asn37 and Asn296 and, like the human and mouse heparanase contains a putative transmembrane region encompassed by residues 352–371. Alignment of the rat heparanase amino acid sequence with that of the human and mouse reveals 79.7% and 93.7% identity respectively (FIG. 6).

A clone of the rat heparanase cDNA fragment (designated rahep-pCR2.1/1) was generated by subcloning the PCR fragment into the vector pCR2.1. The nucleotide sequence of this clone was identical to the sequence determined from the direct sequencing of the PCR product.

EXAMPLE 7

Baculovirus Expression of Mammalian Heparanase
(1) Rat and Mouse Heparanases

Both the rat and mouse heparanases (N-terminal coding sequences) were excised from their respective cloning vectors (rahep-pCR2.1/1 and muhep-pCR2.1/1) using the restriction enzymes EcoRI (mouse cloning) and BamHI/EcoRI (rat clone). The excised fragments were cloned into the plasmid pFastBac (Gibco BRL) in front of the polyhedron promoter and transferred into the bacterial strain DH10Bac. Bacmid DNA (pFastBac integrated into the DH10Bac genome) was prepared and used to transfect Sf9 (*Spodoptera frugiperda*) insect cells. After 72 hours incubation the supernatant and the cells were harvested and used to test for enzyme activity.

Activity observed from the transfected cells versus untransfected cells for 2–3 separate samples is provided in Table 6.

Marginal heparanase activity was observed in ⅓ of the rat and mouse clones expressing the N-terminal truncated sequence.

(2) Human N-terminal and Full length Heparanases

The two human constructs were excised from their respective T-tailed cloning vectors (NH2-pCR2.1 and Full-pCR2.1) using the restriction enzyme EcoRI. The excised fragments were cloned into the plasmid pFastBac (Gibco BRL) in front of the polyhedron promotor and transferred into the bacterial strain DH10Bac. Bacmid DNA (pFastBac integrated into the DH10Bac genome) was prepared and used to transfect Sf9 (*Spodoptera frugiperda*) insect cells. After 72 hours incubation the supernatant and the cells were harvested and used to test for enzyme activity.

Activity observed from the transfected cells versus untrasfected cells for 2–5 separate samples is provided in Table 7.

Clean heparanase activity was observed in ⅗ clones containing the full length human heparanase sequence. Marginal heparanase activity was detected in ⅖ clones containing the N-terminal truncated sequence. Collectively, the baculovirus expression data suggests that the full length heparanase sequence is required to obtain best expression of active haparanase.

EXAMPLE 8

Based on the comparative amino acid sequence data presented in FIG. 6, a number of sequence differences were identified which could be used to prepare peptides for the raising of heparanase-specific antibodies. By way of exemplification only, a 15 amino acid peptide was synthesised that contained sequence differences between the human and mouse/rat heparanase sequences and contained a C-terminal cysteine residue which facilitated coupling of the peptide to a protein carrier prior to immunizing rabbits. The amino acid sequences of the peptide, which spans residues 423 to 437 of the full length human heparanase sequence, is shown below:

VQGSKRRKLRVYLHC (<400>23)

The 15 amino acid peptide was coupled to key hole limpet haemocyanin (KLH) via its C-terminal cysteine residue using Imject maleimide activated KLH (Pierce, Rockford, Ill.) according to the manufacturers instructions. The KLH-peptide conjugate dissolved in PBS (0.2 mg/ml) was emulsified in Freund's Complete Adjuvant (FCA) at a 1:1 ratio of conjugate solution to FCA. Rabbits were immunized subcut in four sites with 0.2 mg of KLH-peptide and the immunization repeated twice at 4 weekly intervals but using Freund's Incomplete Adjuvant rather than FCA, with rabbits being bled 2 weeks after the final immunization and the serum collected.

An ELISA assay was developed for assaying for anti-human heparanase antibodies. The assay involved immobilising human platelet heparanase (5 μg/ml in PBS, 15 hr, 4° C.), purified from human platelets as previously described, in 96 well plastic microplates (25 μl/well). Non-specific binding sites were then blocked by the addition of 200 μl/well of PBS containing 1% (w/v) bovine serum albumin (BSA) for 2 hr at 4° C. Following three washes with 200 μl/well of PBS/0/05% Tween 20 (PBST), 50 μl/well of serial dilutions of the antisera in PBS/1% BSA were added and incubated for 2 hr at 4° C. Following three washes with PBST, 50 μL/well of horse radish peroxidase (HRP) coupled sheep anti-rabbit Ig was added in PBS/1% BSA for 1 hr at 4° C., the plate again washed three times with PBST, and bound HRP measured by the addition of the colourometric HRP substrate 2,2'-azino-bis (3-ethylbenthiazoline-6-sulfonic acid diammonium salt (ABTS), colour development being measured at 405 nm on an ELISA plate reader after 30 minutes incubation at 37° C.

Figure 7:
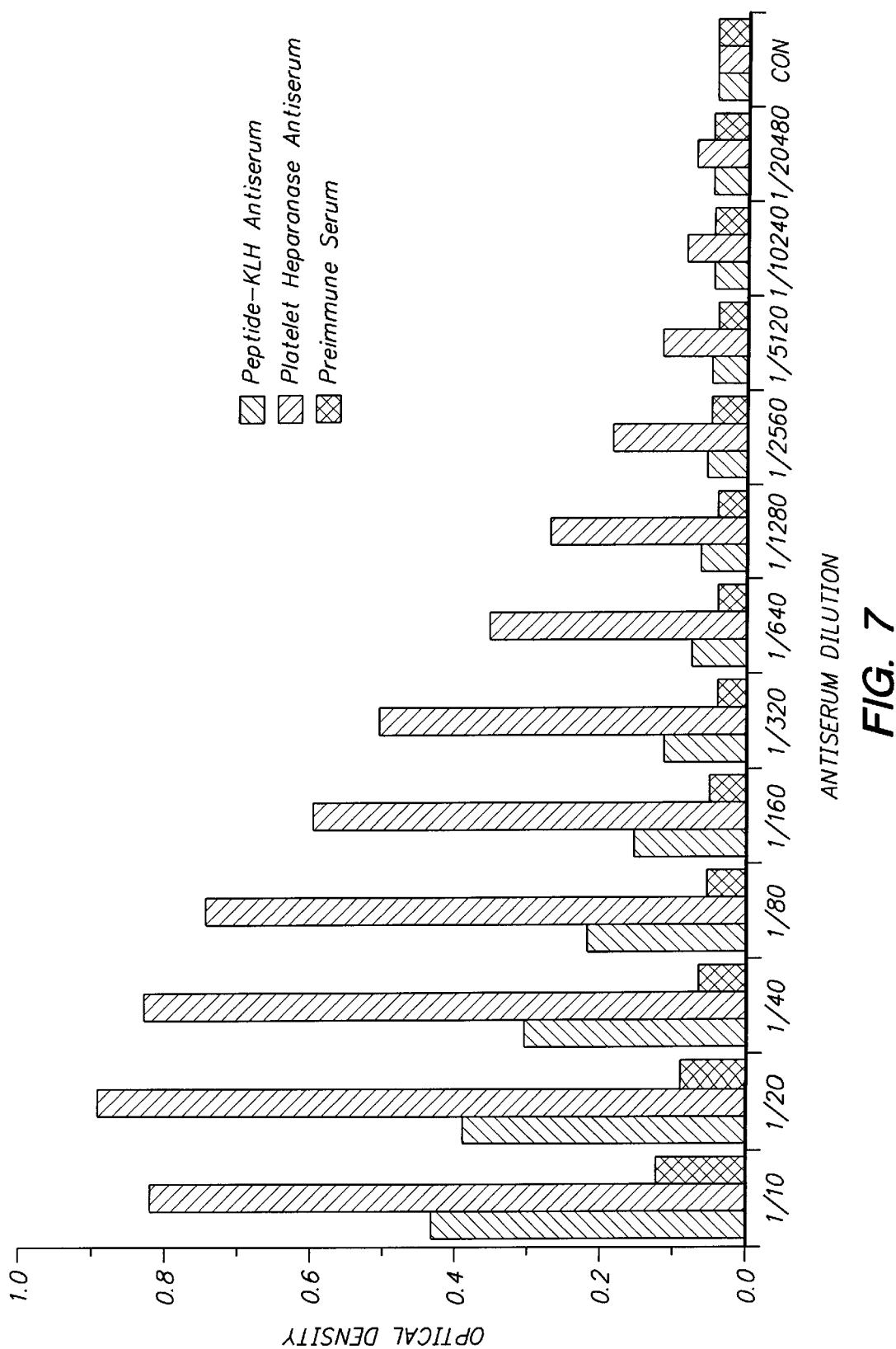
FIG. 7 is a copy of a graphical representation showing the ELISA titres of antisera obtained using a 15-amino acid-long peptide derived from residues 423 to 437 of human heparanase (<400>23) and conjugated to KLH (filled bars) compared to antisera obtained using platelet-derived heparanase (diagonal cross-hatched bars) or compared to preimmune serum obtained from rabbits prior to peptide-KLH immunization (horizontal cross-hatched bars). Data show the optical density (y-axis) for each serum dilution tested (x-axis). Samples marked CON is a non-serum control sample.

FIG. 7 compares the ELISA results obtained with the anti-peptide antiserum with the reactivity of a polyclonal rabbit antibody raised against the purified human platelet heparanase. As shown in FIG. 7, the anti-peptide antiserum exhibits considerable reactivity against the native enzyme, giving an endpoint titre of approx $1/640$, compared with a titre of approx $1/10240$ for the antiserum against the native enzyme. By comparison, serum obtained from rabbits prior to immunization with the peptide-KLH conjugate show negligible reactivty with the human heparanase.

TABLE 3

Sequences of Peptides Isolated from a Proteolytic Digest of Human Platelet Heparanase

| Peptide | Sequence | Comments |
|---|---|---|
| 1. (10aa)[a] | LYGPDVGQPR | Reliable sequeuce |
| 2. (12aa) | VFQVVESTRPGK | Reliable sequence |
| 3. (11aa) | VFQVVESTRPG | Reliable sequence (sample as peptide 2 less residue 12) |
| 4. (7aa) | LPYQVQD | Mainly reliable sequence (? residue 4) |
| 5. (7aa) | AGCQFIP | Minor sequence with peptide 4 |
| 6. (9aa) | LPYLFINLV | Reliable sequence |
| 7. (8aa) | QNDPEDQL | Minor sequence with peptide 6 |
| 8. (8aa) | LYGPDVGQ | Reliable sequence (but incomplete). Same as peptide 1. |
| 9. (12aa) | YLLRPLGPHEIN | Mainly reliable sequence (? residue 3) |
| 10. (11aa) | V(Y/A)(L/A)HNTNTDNP | Mainly reliable sequence although reduced signal in later residues (residue 4 onwards). Polymorphism at residues 2 and 3. |
| 11. (17aa)[b] | KKFKXSTYSRRSVDVLY | Amino-terminal sequence of enzyme |

[a]Number of amino acids (aa) in peptide
[b]Amino-terminal sequence of complete heparanase enzyme prior to proteolytic digestion.

TABLE 4

ESTs corresponding to mouse heparanase in Genbank

| EST Accession No. | Tissue of Origin |
|---|---|
| 620141 | spleen |
| 1177651 | mammary gland |
| 476953 | embryo |
| 522550 | skin |
| 1092868 | diaphragm |

TABLE 5

Oligonucleotides used in cloning mouse and rat heparanase cDNAs

| Oligo-nucleotide | Sequence |
|---|---|
| BamHepN(<400>20) | 5'-AAAAAAGTTCAAGAACAGC-3' |
| mhep3(<400>21) | 5'-CGAAGCTCTGGAACTCG-3' |
| dT-Not(<400>22) | 5'-AACTGGAAGAATTCGCGGCCGCAGGAAT-3' |

TABLE 6

Recombinant Heparanase Expression in *Spodoptera frugiperda* cells Transfected with Mammalain cDNA Clones

| Heparanase cDNA | Heparanase Activity (pmol/hr/$10^6$) cells | | |
|---|---|---|---|
| Mouse | 0.44 | 0.60 | 0.47 |
| Rat | 0.40 | 0.55 | 0.27 |
| Control | 0.27 | 0.42 | |

TABLE 7

Recombinant Heparanase Activity in *Spodoptera frugiperda* Cells Transfected with Full-lenth and Truncated Human Heparanase cDNA Clones

| Gene Fragment | Heparanase Activity (pmol/hr/$10^6$) cells | | | | |
|---|---|---|---|---|---|
| Human (NH2 truncated) | 0.46 | 0.39 | 0.50 | 0 57 | 0.43 |
| Human (Full-length) | 0.22 | 0.97 | 1.12 | 0.76 | 0.39 |
| Control | 0.27 | 0.42 | | | |

REFERENCES

Amann and Brosius (1985). *Gene* 40, 183.

Ausubel, F. M., Brent, R., Kingston, R E, Moore, D. D., Seidman, J. G., Smith, J. A., and Struhl, K. 1987. In: Current Protocols in Molecular Biology, Wiley Interscience (ISBN 047150338).

Bartlett, M. R., Underwood, P. A. and Parish, C. R. (1995a). Immunol. Cell Biol. 73, 113–124.

Bartlett, M. R., Cowden, W. C. and Parish, C. R. (1995b). J. Leukocyte. Biol. 57, 207–213.

Castellot Jr., J. J., Favreau, L. V. Karnovsky, M. J. and Rosenberg, R. D. (1982) J. Biol. Chem. 257, 11256–11260.

Crissman, J. D., Hatfield, J., Shaldenbrand, M., Sloane, B. F. and Honn, K. V. (1985). Lab. Invest 53, 470–478.

Devereux, J., Haeberli, P. and Smithies, O. (1984). *Nucl. Acids Res.* 12:387–395.

Gamse, G., Fromme, H. G. and Kresse, H. (1978). Biochem. Biophys. Acta. 544, 514–528.

Graham, L. D. and Underwood, P. A. (1996). Biochem. Mol. Biol. Int. 39, 563–571.

Haseloff, J. and Gerlach, W. L. (1988). Nature 334, 586–594.

Hellman, U., Wernstedt, C., Gonez, J. and Heldin, C-H. (1985). Anal. Biochem. 224, 451–455.

Hennes, R., Frantzen, F., Keller, R., Schirrmacher, V. and Schwartz-Albiez, R. (1988). Br. J. Cancer. 58, 186–188.

Hoogewerf, A. J., Leone, J. W., Reardon, I. M., Howe, W. J., Asa, D., Heinrikson, R. L. and Ledbetter, S. R. (1995). J. Biol. Chem. 270, 3268–3277.

McPherson, M. J., Quirke, P. and Taylor, G. R. (1991) PCR A Practical Approach. IRL Press, Oxford Univerity Press, Oxford, United Kingdom.

Messer, M., Rismiller, P. R., Griffiths, M. and Shaw, D. C. (1997) Comp. Biochem. Physiol. (In Press).

Nakajima, M., Irimura, T., Di Ferrante, D., Di Ferrante, N., and Nicolson, G. L. (1983). Science 220, 611–613.

Needleman and Wunsch (1970) J. Mol. Biol. 48:443–453.

Sambrook, J., E. F. Fritsch, and T. Maniatis (1989) Molecular cloning. A laboratory manual. Second edition. Cold Spring Harbour Laboratory, Cold Spring Harbour, N.Y.

Schmitt, M., Janicke, F., and Graeff, J. (1992). Fibrinolysis. 6 (Suppl 4), 3–26.

Shimatake and Rosenberg (1981) *Nature* 292, 128.

Studier and Moffat (1986) J. Mol. Biol. 189, 113.

Tanaka, N. G., Tohgo, A. and Ogawa, H. (1986). Invasion Metastasis. 6, 209–217. Thompson, J. D., Higgins, D. G., and Gibson, T. J. (1994) *Nucl. Acids Res.* 22:4673–4680.

Turnbull, J. E., and Gallagher, J. T. (1990). Biochem. J. 265, 715–724.

Turnbull, J. E., and Gallagher, J. T. (1991). Biochem. J. 273, 553–559.

Vlodavsky, I., Eldor, A., Haimovitz-Friedman, A., Matzner, Y., Ishai-Michaeli, R., Lider, O., Naparstek, Y., Cohen, I. R., and Fuks, Z. (1992). Invasion Metastasis 12, 112–127.

Wasteson, A., Hook, M. and Westermark, B. (1976). 64, 218–221.

Wateson, A., Glimelius, B., Busch, C., Westermark, B., Heldin, C-H and Norling, B. (1977). Thromb. Res. 11, 309–321.

Yahalom, J., Eldor, A., Fuks, Z. and Vlodavsky, I. (1984). J. Clin. Invest. 74, 1842–1849.

Yahalom, J., Eldor, A. Biran, S., Fuks, Z. and Vlodavsky, I. (1985). Radiother. Oncol. 3, 211–225.

Yurchenco, P. D., and Schittny, J. C. (1990). FASEB J. 4, 1577–1590.

We claim:

1. An isolated nucleic acid molecule comprising the nucleotide sequence set forth in SEQ ID NO.: 12 which encodes a polypeptide having mammalian heparanase activity or a complementary nucleotide sequence thereto.

2. An isolated nucleic acid molecule comprising the nucleotide sequence set forth in SEQ ID NO.: 16 which encodes a polypeptide having mammalian heparanase activity or a complementary nucleotide sequence thereto.

3. An isolated nucleic acid molecule comprising the nucleotide sequence set forth in SEQ ID NO.: 18 which encodes a polypeptide having mammalian heparanase activity, or a complementary nucleotide sequence thereto.

4. An isolated nucleic acid molecule encoding a polypeptide having mammalian heparanase activity, wherein said polypeptide has the amino acid sequence set forth in SEQ ID NO.:13.

5. An isolated nucleic acid molecule encoding a polypeptide having mammalian heparanase activity, wherein said polypeptide has the amino acid sequence set forth in SEQ ID NO.:17.

6. An isolated nucleic acid molecule encoding a polypeptide having mammalian heparanase activity, wherein said polypeptide has the amino acid sequence set forth in SEQ ID NO.:19.

7. An expression vector comprising the isolated nucleic acid molecule of claim 1 operably linked to a promoter sequence.

8. The expression vector of claim 7 wherein the promoter is the polyhedron promoter.

9. An expression vector comprising the isolated nucleic acid molecule of claim 2 operably linked to a promoter sequence.

10. The expression vector of claim 9 wherein the promoter is the polyhedron promoter.

11. An expression vector comprising the isolated nucleic acid molecule of claim 3 operably linked to a promoter sequence.

12. The expression vector of claim 11 wherein the promoter is the polyhedron promoter.

13. An expression vector comprising the isolated nucleic acid molecule of claim 4 operably linked to a promoter sequence.

14. The expression vector of claim 13 wherein the promoter is the polyhedron promoter.

15. An expression vector comprising the isolated nucleic acid molecule of claim 5 operably linked to a promoter sequence.

16. The expression vector of claim 15 wherein the promoter is the polyhedron promoter.

17. An expression vector comprising the isolated nucleic acid molecule of claim 6 operably linked to a promoter sequence.

18. The expression vector of claim 17 wherein the promoter is the polyhedron promoter.

19. A host cell comprising the expression vector of claim 7.

20. The host cell of claim 19, wherein the cell is an insect cell.

21. A host cell comprising the expression vector of claim 9.

22. The host cell of claim 21, wherein the cell is an insect cell.

23. A host cell comprising the expression vector of claim 11.

24. The host cell of claim 23, wherein the cell is an insect cell.

25. A host cell comprising the expression vector of claim 13.

26. The host cell of claim 25, wherein the cell is an insect cell.

27. A host cell comprising the expression vector of claim 15.

28. The host cell of claim 27, wherein the cell is an insect cell.

29. A host cell comprising the expression vector of claim 17.

30. The host cell of claim 29, wherein the cell is an insect cell.

31. A heparanase expression product of the host cell of claim 19.

32. A heparanase expression product of the host cell of claim 21.

33. A heparanase expression product of the host cell of claim 23.

34. A heparanase expression product of the host cell of claim 25.

35. A heparanase expression product of the host cell of claim 27.

36. A heparanase expression product of the host cell of claim 29.

* * * * *

SEQUENCE LISTING

```
<160> NUMBER OF SEQ ID NOS: 23

<210> SEQ ID NO: 1
<211> LENGTH: 10
<212> TYPE: PRT
<213> ORGANISM: Artificial Sequence
<220> FEATURE:
<223> OTHER INFORMATION: Description of Artificial Sequence: PEPTIDE

<400> SEQUENCE: 1

Leu Tyr Gly Pro Asp Val Gly Gln Pro Arg
 1               5                   10
```

```
<210> SEQ ID NO: 2
<211> LENGTH: 12
<212> TYPE: PRT
<213> ORGANISM: Artificial Sequence
<220> FEATURE:
<223> OTHER INFORMATION: Description of Artificial Sequence: PEPTIDE

<400> SEQUENCE: 2

Val Phe Gln Val Val Glu Ser Thr Arg Pro Gly Lys
 1               5                  10

<210> SEQ ID NO: 3
<211> LENGTH: 11
<212> TYPE: PRT
<213> ORGANISM: Artificial Sequence
<220> FEATURE:
<223> OTHER INFORMATION: Description of Artificial Sequence: PEPTIDE

<400> SEQUENCE: 3

Val Phe Gln Val Val Glu Ser Thr Arg Pro Gly
 1               5                  10

<210> SEQ ID NO: 4
<211> LENGTH: 7
<212> TYPE: PRT
<213> ORGANISM: Artificial Sequence
<220> FEATURE:
<223> OTHER INFORMATION: Description of Artificial Sequence: PEPTIDE

<400> SEQUENCE: 4

Leu Pro Tyr Gln Val Gln Asp
 1               5

<210> SEQ ID NO: 5
<211> LENGTH: 7
<212> TYPE: PRT
<213> ORGANISM: Artificial Sequence
<220> FEATURE:
<223> OTHER INFORMATION: Description of Artificial Sequence: PEPTIDE

<400> SEQUENCE: 5

Ala Gly Cys Gln Phe Ile Pro
 1               5

<210> SEQ ID NO: 6
<211> LENGTH: 9
<212> TYPE: PRT
<213> ORGANISM: Artificial Sequence
<220> FEATURE:
<223> OTHER INFORMATION: Description of Artificial Sequence: PEPTIDE

<400> SEQUENCE: 6

Leu Pro Tyr Leu Phe Ile Asn Leu Val
 1               5

<210> SEQ ID NO: 7
<211> LENGTH: 8
<212> TYPE: PRT
<213> ORGANISM: Artificial Sequence
<220> FEATURE:
<223> OTHER INFORMATION: Description of Artificial Sequence: PEPTIDE

<400> SEQUENCE: 7

Gln Asn Asp Pro Glu Asp Gln Leu
 1               5

<210> SEQ ID NO: 8
```

<211> LENGTH: 8
<212> TYPE: PRT
<213> ORGANISM: Artificial Sequence
<220> FEATURE:
<223> OTHER INFORMATION: Description of Artificial Sequence: PEPTIDE

<400> SEQUENCE: 8

Leu Tyr Gly Pro Asp Val Gly Gln
 1               5

<210> SEQ ID NO: 9
<211> LENGTH: 12
<212> TYPE: PRT
<213> ORGANISM: Artificial Sequence
<220> FEATURE:
<223> OTHER INFORMATION: Description of Artificial Sequence: PEPTIDE

<400> SEQUENCE: 9

Tyr Leu Leu Arg Pro Leu Gly Pro His Glu Ile Asn
 1               5                  10

<210> SEQ ID NO: 10
<211> LENGTH: 11
<212> TYPE: PRT
<213> ORGANISM: Artificial Sequence
<220> FEATURE:
<223> OTHER INFORMATION: Description of Artificial Sequence: PEPTIDE

<400> SEQUENCE: 10

Val Tyr Leu His Asn Thr Asn Thr Asp Asn Pro
 1               5                  10

<210> SEQ ID NO: 11
<211> LENGTH: 16
<212> TYPE: PRT
<213> ORGANISM: Artificial Sequence
<220> FEATURE:
<223> OTHER INFORMATION: Description of Artificial Sequence: PEPTIDE
<220> FEATURE:
<221> NAME/KEY: PEPTIDE
<222> LOCATION: (5)
<223> OTHER INFORMATION: Amino acid 5 is Xaa wherein Xaa = any amino
      acid.

<400> SEQUENCE: 11

Lys Lys Phe Lys Xaa Ser Thr Tyr Ser Arg Arg Ser Val Asp Val Leu
 1               5                  10                  15

<210> SEQ ID NO: 12
<211> LENGTH: 1713
<212> TYPE: DNA
<213> ORGANISM: Homo sapiens
<220> FEATURE:
<221> NAME/KEY: CDS
<222> LOCATION: (46)..(1674)
<220> FEATURE:
<221> NAME/KEY: mat_peptide
<222> LOCATION: (517)..(1674)

<400> SEQUENCE: 12
ccgctgcgcg gcagctggcg gggggagcag ccaggtgagc ccaag atg ctg ctg cgc     57
                                                Met Leu Leu Arg
                                                    -155 tcg aag cct gcg ctg ccg ccg ccg ctg atg ctg ctg ctc ctg ggg ccg     105
Ser Lys Pro Ala Leu Pro Pro Pro Leu Met Leu Leu Leu Leu Gly Pro
        -150             -145                 -140 ctg ggt ccc ctc tcc cct ggt gcc ctg ccc cga cct gcg caa gca cag     153
Leu Gly Pro Leu Ser Pro Gly Ala Leu Pro Arg Pro Ala Gln Ala Gln -continued

```
           -135                -130                -125
gac gtc gtg gac ctg gac ttc ttc acc cag gag ccg ctg cac ctg gtg     201
Asp Val Val Asp Leu Asp Phe Phe Thr Gln Glu Pro Leu His Leu Val
    -120                -115                -110 agc ccc tcg ttc ctg tcc gtc acc att gac gcc aac ctg gcc acg gac     249
Ser Pro Ser Phe Leu Ser Val Thr Ile Asp Ala Asn Leu Ala Thr Asp
-105                -100                -95                 -90 ccg cgg ttc ctc atc ctc ctg ggt tct cca aag ctt cgt acc ttg gcc     297
Pro Arg Phe Leu Ile Leu Leu Gly Ser Pro Lys Leu Arg Thr Leu Ala
                -85                 -80                 -75 aga ggc ttg tct cct gcg tac ctg agg ttt ggt ggc acc aag aca gac     345
Arg Gly Leu Ser Pro Ala Tyr Leu Arg Phe Gly Gly Thr Lys Thr Asp
            -70                 -65                 -60 ttc cta att ttc gat ccc aag aag gaa tca acc ttt gaa gag aga agt     393
Phe Leu Ile Phe Asp Pro Lys Lys Glu Ser Thr Phe Glu Glu Arg Ser
        -55                 -50                 -45 tac tgg caa tct caa gtc aac cag gat att tgc aaa tat gga tcc atc     441
Tyr Trp Gln Ser Gln Val Asn Gln Asp Ile Cys Lys Tyr Gly Ser Ile
    -40                 -35                 -30 cct cct gat gtg gag gag aag tta cgg ttg gaa tgg ccc tac cag gag     489
Pro Pro Asp Val Glu Glu Lys Leu Arg Leu Glu Trp Pro Tyr Gln Glu
-25                 -20                 -15                 -10 caa ttg cta ctc cga gaa cac tac cag aaa aag ttc aag aac agc acc     537
Gln Leu Leu Leu Arg Glu His Tyr Gln Lys Lys Phe Lys Asn Ser Thr
                -5                  -1  1                   5 tac tca aga agc tct gta gat gtg cta tac act ttt gca aac tgc tca     585
Tyr Ser Arg Ser Ser Val Asp Val Leu Tyr Thr Phe Ala Asn Cys Ser
            10                  15                  20 gga ctg gac ttg atc ttt ggc cta aat gcg tta tta aga aca gca gat     633
Gly Leu Asp Leu Ile Phe Gly Leu Asn Ala Leu Leu Arg Thr Ala Asp
        25                  30                  35 ttg cag tgg aac agt tct aat gct cag ttg ctc ctg gac tac tgc tct     681
Leu Gln Trp Asn Ser Ser Asn Ala Gln Leu Leu Leu Asp Tyr Cys Ser
    40                  45                  50                  55 tcc aag ggg tat aac att tct tgg gaa cta ggc aat gaa cct aac agt     729
Ser Lys Gly Tyr Asn Ile Ser Trp Glu Leu Gly Asn Glu Pro Asn Ser
                60                  65                  70 ttc ctt aag aag gct gat att ttc atc aat ggg tcg cag tta gga gaa     777
Phe Leu Lys Lys Ala Asp Ile Phe Ile Asn Gly Ser Gln Leu Gly Glu
            75                  80                  85 gat ttt att caa ttg cat aaa ctt cta aga aag tcc acc ttc aaa aat     825
Asp Phe Ile Gln Leu His Lys Leu Leu Arg Lys Ser Thr Phe Lys Asn
        90                  95                  100 gca aaa ctc tat ggt cct gat gtt ggt cag cct cga aga aag acg gct     873
Ala Lys Leu Tyr Gly Pro Asp Val Gly Gln Pro Arg Arg Lys Thr Ala
    105                 110                 115 aag atg ctg aag agc ttc ctg aag gct ggt gga gaa gtg att gat tca     921
Lys Met Leu Lys Ser Phe Leu Lys Ala Gly Gly Glu Val Ile Asp Ser
120                 125                 130                 135 gtt aca tgg cat cac tac tat ttg aat gga cgg act gct acc agg gaa     969
Val Thr Trp His His Tyr Tyr Leu Asn Gly Arg Thr Ala Thr Arg Glu
                140                 145                 150 gat ttt cta aac cct gat gta ttg gac att ttt att tca tct gtg caa    1017
Asp Phe Leu Asn Pro Asp Val Leu Asp Ile Phe Ile Ser Ser Val Gln
            155                 160                 165 aaa gtt ttc cag gtg gtt gag agc acc agg cct ggc aag aag gtc tgg    1065
Lys Val Phe Gln Val Val Glu Ser Thr Arg Pro Gly Lys Lys Val Trp
        170                 175                 180 tta gga gaa aca agc tct gca tat gga ggc gga gcg ccc ttg cta tcc    1113
```

```
                                                                    -continued Leu Gly Glu Thr Ser Ser Ala Tyr Gly Gly Ala Pro Leu Leu Ser
        185                 190                 195 gac acc ttt gca gct ggc ttt atg tgg ctg gat aaa ttg ggc ctg tca      1161
Asp Thr Phe Ala Ala Gly Phe Met Trp Leu Asp Lys Leu Gly Leu Ser
200                 205                 210                 215 gcc cga atg gga ata gaa gtg gtg atg agg caa gta ttc ttt gga gca      1209
Ala Arg Met Gly Ile Glu Val Val Met Arg Gln Val Phe Phe Gly Ala
                220                 225                 230 gga aac tac cat tta gtg gat gaa aac ttc gat cct tta cct gat tat      1257
Gly Asn Tyr His Leu Val Asp Glu Asn Phe Asp Pro Leu Pro Asp Tyr
            235                 240                 245 tgg cta tct ctt ctg ttc aag aaa ttg gtg ggc acc aag gtg tta atg      1305
Trp Leu Ser Leu Leu Phe Lys Lys Leu Val Gly Thr Lys Val Leu Met
        250                 255                 260 gca agc gtg caa ggt tca aag aga agg aag ctt cga gta tac ctt cat      1353
Ala Ser Val Gln Gly Ser Lys Arg Arg Lys Leu Arg Val Tyr Leu His
265                 270                 275 tgc aca aac act gac aat cca agg tat aaa gaa gga gat tta act ctg      1401
Cys Thr Asn Thr Asp Asn Pro Arg Tyr Lys Glu Gly Asp Leu Thr Leu
280                 285                 290                 295 tat gcc ata aac ctc cat aat gtc acc aag tac ttg cgg tta ccc tat      1449
Tyr Ala Ile Asn Leu His Asn Val Thr Lys Tyr Leu Arg Leu Pro Tyr
                300                 305                 310 cct ttt tct aac aag caa gtg gat aaa tac ctt cta aga cct ttg gga      1497
Pro Phe Ser Asn Lys Gln Val Asp Lys Tyr Leu Leu Arg Pro Leu Gly
            315                 320                 325 cct cat gga tta ctt tcc aaa tct gtc caa ctc aat ggt cta act cta      1545
Pro His Gly Leu Leu Ser Lys Ser Val Gln Leu Asn Gly Leu Thr Leu
        330                 335                 340 aag atg gtg gat gat caa acc ttg cca cct tta atg gaa aaa cct ctc      1593
Lys Met Val Asp Asp Gln Thr Leu Pro Pro Leu Met Glu Lys Pro Leu
345                 350                 355 cgg cca gga agt tca ctg ggc ttg cca gct ttc tca tat agt ttt ttt      1641
Arg Pro Gly Ser Ser Leu Gly Leu Pro Ala Phe Ser Tyr Ser Phe Phe
360                 365                 370                 375 gtg ata aga aat gcc aaa gtt gct gct tgc atc tgaaaataaa atatactagt   1694
Val Ile Arg Asn Ala Lys Val Ala Ala Cys Ile
                380                 385 cctgaaaaaa aaaaaaaa                                                  1713

<210> SEQ ID NO: 13
<211> LENGTH: 543
<212> TYPE: PRT
<213> ORGANISM: Homo sapiens

<400> SEQUENCE: 13

Met Leu Leu Arg Ser Lys Pro Ala Leu Pro Pro Pro Leu Met Leu Leu
        -155                -150                -145

Leu Leu Gly Pro Leu Gly Pro Leu Ser Pro Gly Ala Leu Pro Arg Pro
    -140                -135                -130

Ala Gln Ala Gln Asp Val Val Asp Leu Asp Phe Phe Thr Gln Glu Pro
-125                -120                -115                -110

Leu His Leu Val Ser Pro Ser Phe Leu Ser Val Thr Ile Asp Ala Asn
            -105                -100                -95

Leu Ala Thr Asp Pro Arg Phe Leu Ile Leu Leu Gly Ser Pro Lys Leu
        -90                 -85                 -80

Arg Thr Leu Ala Arg Gly Leu Ser Pro Ala Tyr Leu Arg Phe Gly Gly
    -75                 -70                 -65
```

```
Thr Lys Thr Asp Phe Leu Ile Phe Asp Pro Lys Lys Glu Ser Thr Phe
    -60              -55              -50

Glu Glu Arg Ser Tyr Trp Gln Ser Gln Val Asn Gln Asp Ile Cys Lys
-45              -40              -35                       -30

Tyr Gly Ser Ile Pro Pro Asp Val Glu Glu Lys Leu Arg Leu Glu Trp
                -25              -20                  -15

Pro Tyr Gln Glu Gln Leu Leu Leu Arg Glu His Tyr Gln Lys Lys Phe
            -10               -5              -1   1

Lys Asn Ser Thr Tyr Ser Arg Ser Ser Val Asp Val Leu Tyr Thr Phe
         5              10              15

Ala Asn Cys Ser Gly Leu Asp Leu Ile Phe Gly Leu Asn Ala Leu Leu
 20              25              30                       35

Arg Thr Ala Asp Leu Gln Trp Asn Ser Ser Asn Ala Gln Leu Leu Leu
             40              45                       50

Asp Tyr Cys Ser Ser Lys Gly Tyr Asn Ile Ser Trp Glu Leu Gly Asn
             55              60              65

Glu Pro Asn Ser Phe Leu Lys Lys Ala Asp Ile Phe Ile Asn Gly Ser
         70              75              80

Gln Leu Gly Glu Asp Phe Ile Gln Leu His Lys Leu Leu Arg Lys Ser
     85              90              95

Thr Phe Lys Asn Ala Lys Leu Tyr Gly Pro Asp Val Gly Gln Pro Arg
100             105             110                     115

Arg Lys Thr Ala Lys Met Leu Lys Ser Phe Leu Lys Ala Gly Gly Glu
             120             125                     130

Val Ile Asp Ser Val Thr Trp His His Tyr Tyr Leu Asn Gly Arg Thr
             135             140             145

Ala Thr Arg Glu Asp Phe Leu Asn Pro Asp Val Leu Asp Ile Phe Ile
         150             155             160

Ser Ser Val Gln Lys Val Phe Gln Val Val Glu Ser Thr Arg Pro Gly
     165             170             175

Lys Lys Val Trp Leu Gly Glu Thr Ser Ser Ala Tyr Gly Gly Gly Ala
180             185             190                     195

Pro Leu Leu Ser Asp Thr Phe Ala Ala Gly Phe Met Trp Leu Asp Lys
                200             205             210

Leu Gly Leu Ser Ala Arg Met Gly Ile Glu Val Val Met Arg Gln Val
             215             220             225

Phe Phe Gly Ala Gly Asn Tyr His Leu Val Asp Glu Asn Phe Asp Pro
         230             235             240

Leu Pro Asp Tyr Trp Leu Ser Leu Phe Lys Lys Leu Val Gly Thr
         245             250             255

Lys Val Leu Met Ala Ser Val Gln Gly Ser Lys Arg Arg Lys Leu Arg
260             265             270                     275

Val Tyr Leu His Cys Thr Asn Thr Asp Asn Pro Arg Tyr Lys Glu Gly
             280             285             290

Asp Leu Thr Leu Tyr Ala Ile Asn Leu His Asn Val Thr Lys Tyr Leu
         295             300             305

Arg Leu Pro Tyr Pro Phe Ser Asn Lys Gln Val Asp Lys Tyr Leu Leu
         310             315             320

Arg Pro Leu Gly Pro His Gly Leu Leu Ser Lys Ser Val Gln Leu Asn
         325             330             335

Gly Leu Thr Leu Lys Met Val Asp Asp Gln Thr Leu Pro Pro Leu Met
340             345             350             355

Glu Lys Pro Leu Arg Pro Gly Ser Ser Leu Gly Leu Pro Ala Phe Ser
```

```
                360             365             370
Tyr Ser Phe Phe Val Ile Arg Asn Ala Lys Val Ala Ala Cys Ile
            375             380             385

<210> SEQ ID NO: 14
<211> LENGTH: 1723
<212> TYPE: DNA
<213> ORGANISM: Homo sapiens
<220> FEATURE:
<221> NAME/KEY: CDS
<222> LOCATION: (52)..(1647)

<400> SEQUENCE: 14
ggcgggccgc tgcgcggcag ctggcggggg gagcagccag gtgagcccaa g atg ctg      57
                                                         Met Leu
                                                           1 ctg cgc tcg aag cct gcg ctg ccg ccg ccg ctg atg ctg ctc ctg          105
Leu Arg Ser Lys Pro Ala Leu Pro Pro Pro Leu Met Leu Leu Leu
         5                  10                  15 ggg ccg ctg ggt ccc ctc tcc cct ggc gcc ctg ccc cga cct gcg caa      153
Gly Pro Leu Gly Pro Leu Ser Pro Gly Ala Leu Pro Arg Pro Ala Gln
    20                  25                  30 gca cag gac gtc gtg gac ctg gac ttc ttc acc cag gag ccg ctg cac      201
Ala Gln Asp Val Val Asp Leu Asp Phe Phe Thr Gln Glu Pro Leu His
 35                  40                  45                  50 ctg gtg agc ccc tcg ttc ctg tcc gtc acc att gac gcc aac ctg gcc      249
Leu Val Ser Pro Ser Phe Leu Ser Val Thr Ile Asp Ala Asn Leu Ala
                 55                  60                  65 acg gac ccg cgg ttc ctc atc ctc ctg ggt tct cca aag ctt cgt acc      297
Thr Asp Pro Arg Phe Leu Ile Leu Leu Gly Ser Pro Lys Leu Arg Thr
             70                  75                  80 ttg gcc aga ggc ttg tct cct gcg tac ctg agg ttt ggt ggc acc aag      345
Leu Ala Arg Gly Leu Ser Pro Ala Tyr Leu Arg Phe Gly Gly Thr Lys
         85                  90                  95 aca gac ttc cta att ttc gat ccc aag aag gaa tca acc ttt gaa gag      393
Thr Asp Phe Leu Ile Phe Asp Pro Lys Lys Glu Ser Thr Phe Glu Glu
    100                 105                 110 aga agt tac tgg caa tct caa gtc aac cag gat att tgc aaa tat gga      441
Arg Ser Tyr Trp Gln Ser Gln Val Asn Gln Asp Ile Cys Lys Tyr Gly
115                 120                 125                 130 tcc atc cct cct gat gtg gag gag aag tta cgg ttg gaa tgg ccc tac      489
Ser Ile Pro Pro Asp Val Glu Glu Lys Leu Arg Leu Glu Trp Pro Tyr
                135                 140                 145 cag gag caa ttg cta ctc cga gaa cac tac cag aaa aag ttc aag aac      537
Gln Glu Gln Leu Leu Leu Arg Glu His Tyr Gln Lys Lys Phe Lys Asn
            150                 155                 160 agc acc tac tca aga agc tct gta gat gtg cta tac act ttt gca aac      585
Ser Thr Tyr Ser Arg Ser Ser Val Asp Val Leu Tyr Thr Phe Ala Asn
        165                 170                 175 tgc tca gga ctg gac ttg atc ttt ggc cta aat gcg tta tta aga aca      633
Cys Ser Gly Leu Asp Leu Ile Phe Gly Leu Asn Ala Leu Leu Arg Thr
    180                 185                 190 gca gat ttg cag tgg aac agt tct aat gct cag ttg ctc ctg gac tac      681
Ala Asp Leu Gln Trp Asn Ser Ser Asn Ala Gln Leu Leu Leu Asp Tyr
195                 200                 205                 210 tgc tct tcc aag ggg tat aac att tct tgg gaa cta ggc aat gaa cct      729
Cys Ser Ser Lys Gly Tyr Asn Ile Ser Trp Glu Leu Gly Asn Glu Pro
                215                 220                 225 aac agt ttc ctt aag aag gct gat att ttc atc aat ggg tcg cag tta      777
Asn Ser Phe Leu Lys Lys Ala Asp Ile Phe Ile Asn Gly Ser Gln Leu
            230                 235                 240
```

```
gga gaa gat ttt att caa ttg cat aaa ctt cta aga aag tcc acc ttc     825
Gly Glu Asp Phe Ile Gln Leu His Lys Leu Leu Arg Lys Ser Thr Phe
        245                 250                 255 aaa aat gca aaa ctc tat ggt cct gat gtt ggt cag cct cga aga aag     873
Lys Asn Ala Lys Leu Tyr Gly Pro Asp Val Gly Gln Pro Arg Arg Lys
        260                 265                 270 acg gct aag atg ctg aag agc ttc ctg aag gct ggt gga gaa gtg att     921
Thr Ala Lys Met Leu Lys Ser Phe Leu Lys Ala Gly Gly Glu Val Ile
275                 280                 285                 290 gat tca gtt aca tgg cat cac tac tat ttg aat gga cgg act gct acc     969
Asp Ser Val Thr Trp His His Tyr Tyr Leu Asn Gly Arg Thr Ala Thr
                    295                 300                 305 agg gaa gat ttt cta aac cct gat gta ttg gac att ttt att tca tct    1017
Arg Glu Asp Phe Leu Asn Pro Asp Val Leu Asp Ile Phe Ile Ser Ser
                310                 315                 320 gtg caa aaa gtt ttc cag gtg gtt gag agc acc agg cct ggc aag aag    1065
Val Gln Lys Val Phe Gln Val Val Glu Ser Thr Arg Pro Gly Lys Lys
            325                 330                 335 gtc tgg tta gga gaa aca agc tct gca tat gga ggc gga gcg ccc ttg    1113
Val Trp Leu Gly Glu Thr Ser Ser Ala Tyr Gly Gly Gly Ala Pro Leu
        340                 345                 350 cta tcc gac acc ttt gca gct ggc ttt atg tgg ctg gat aaa ttg ggc    1161
Leu Ser Asp Thr Phe Ala Ala Gly Phe Met Trp Leu Asp Lys Leu Gly
355                 360                 365                 370 ctg tca gcc cga atg gga ata gaa gtg gtg atg agg caa gta ttc ttt    1209
Leu Ser Ala Arg Met Gly Ile Glu Val Val Met Arg Gln Val Phe Phe
                    375                 380                 385 gga gca gga aac tac cat tta gtg gat gaa aac ttc gat cct tta cct    1257
Gly Ala Gly Asn Tyr His Leu Val Asp Glu Asn Phe Asp Pro Leu Pro
                390                 395                 400 gat tat tgg cta tct ctt ctg ttc aag aaa ttg gtg ggc acc aag gtg    1305
Asp Tyr Trp Leu Ser Leu Leu Phe Lys Lys Leu Val Gly Thr Lys Val
            405                 410                 415 tta atg gca agc gtg caa ggt tca aag aga agg aag ctt cga gta tac    1353
Leu Met Ala Ser Val Gln Gly Ser Lys Arg Arg Lys Leu Arg Val Tyr
        420                 425                 430 ctt cat tgc aca aac act gac aat cca agg tat aaa gaa gga gat tta    1401
Leu His Cys Thr Asn Thr Asp Asn Pro Arg Tyr Lys Glu Gly Asp Leu
435                 440                 445                 450 act ctg tat gcc ata aac ctc cat aat gtc acc aag tac ttg cgg tta    1449
Thr Leu Tyr Ala Ile Asn Leu His Asn Val Thr Lys Tyr Leu Arg Leu
                    455                 460                 465 ccc tat cct ttt tct aac aag caa gtg gat aaa tac ctt cta aga cct    1497
Pro Tyr Pro Phe Ser Asn Lys Gln Val Asp Lys Tyr Leu Leu Arg Pro
                470                 475                 480 ttg gga cct cat gga tta ctt tcc aaa tct gtc caa ctc aat ggt cta    1545
Leu Gly Pro His Gly Leu Leu Ser Lys Ser Val Gln Leu Asn Gly Leu
            485                 490                 495 act cta aag atg gtg gat gat caa acc ttg cca cct tta atg gaa aaa    1593
Thr Leu Lys Met Val Asp Asp Gln Thr Leu Pro Pro Leu Met Glu Lys
        500                 505                 510 cct ctc cgg cca gga agt tca ctg ggt tgc cag ctt tct cat ata gtt    1641
Pro Leu Arg Pro Gly Ser Ser Leu Gly Cys Gln Leu Ser His Ile Val
515                 520                 525                 530 ttt ttg tgataagaaa tgccaaagtt gctgcttgca tctgaaaata aaatatacta    1697
Phe Leu gtcctgacac tgaaaaaaaa aaaaaa                                       1723
```

```
<210> SEQ ID NO: 15
<211> LENGTH: 532
<212> TYPE: PRT
<213> ORGANISM: Homo sapiens

<400> SEQUENCE: 15
```

| | | | | | | | | | | | | | | |
|---|---|---|---|---|---|---|---|---|---|---|---|---|---|---|
| Met | Leu | Leu | Arg | Ser | Lys | Pro | Ala | Leu | Pro | Pro | Leu | Met | Leu | Leu |
| 1 | | | | 5 | | | | | 10 | | | | | 15 |
| Leu | Leu | Gly | Pro | Leu | Gly | Pro | Leu | Ser | Pro | Gly | Ala | Leu | Pro | Arg | Pro |
| | | | 20 | | | | | 25 | | | | | 30 | | |
| Ala | Gln | Ala | Gln | Asp | Val | Val | Asp | Leu | Asp | Phe | Phe | Thr | Gln | Glu | Pro |
| | | 35 | | | | | 40 | | | | | 45 | | | |
| Leu | His | Leu | Val | Ser | Pro | Ser | Phe | Leu | Ser | Val | Thr | Ile | Asp | Ala | Asn |
| | 50 | | | | | 55 | | | | | 60 | | | | |
| Leu | Ala | Thr | Asp | Pro | Arg | Phe | Leu | Ile | Leu | Leu | Gly | Ser | Pro | Lys | Leu |
| 65 | | | | | 70 | | | | | 75 | | | | | 80 |
| Arg | Thr | Leu | Ala | Arg | Gly | Leu | Ser | Pro | Ala | Tyr | Leu | Arg | Phe | Gly | Gly |
| | | | | 85 | | | | | 90 | | | | | 95 | |
| Thr | Lys | Thr | Asp | Phe | Leu | Ile | Phe | Asp | Pro | Lys | Lys | Glu | Ser | Thr | Phe |
| | | | 100 | | | | | 105 | | | | | 110 | | |
| Glu | Glu | Arg | Ser | Tyr | Trp | Gln | Ser | Gln | Val | Asn | Gln | Asp | Ile | Cys | Lys |
| | | 115 | | | | | 120 | | | | | 125 | | | |
| Tyr | Gly | Ser | Ile | Pro | Pro | Asp | Val | Glu | Glu | Lys | Leu | Arg | Leu | Glu | Trp |
| 130 | | | | | 135 | | | | | 140 | | | | | |
| Pro | Tyr | Gln | Glu | Gln | Leu | Leu | Leu | Arg | Glu | His | Tyr | Gln | Lys | Lys | Phe |
| 145 | | | | | 150 | | | | | 155 | | | | | 160 |
| Lys | Asn | Ser | Thr | Tyr | Ser | Arg | Ser | Ser | Val | Asp | Val | Leu | Tyr | Thr | Phe |
| | | | | 165 | | | | | 170 | | | | | 175 | |
| Ala | Asn | Cys | Ser | Gly | Leu | Asp | Leu | Ile | Phe | Gly | Leu | Asn | Ala | Leu | Leu |
| | | | 180 | | | | | 185 | | | | | 190 | | |
| Arg | Thr | Ala | Asp | Leu | Gln | Trp | Asn | Ser | Ser | Asn | Ala | Gln | Leu | Leu | Leu |
| | | 195 | | | | | 200 | | | | | 205 | | | |
| Asp | Tyr | Cys | Ser | Ser | Lys | Gly | Tyr | Asn | Ile | Ser | Trp | Glu | Leu | Gly | Asn |
| | 210 | | | | | 215 | | | | | 220 | | | | |
| Glu | Pro | Asn | Ser | Phe | Leu | Lys | Lys | Ala | Asp | Ile | Phe | Ile | Asn | Gly | Ser |
| 225 | | | | | 230 | | | | | 235 | | | | | 240 |
| Gln | Leu | Gly | Glu | Asp | Phe | Ile | Gln | Leu | His | Lys | Leu | Leu | Arg | Lys | Ser |
| | | | | 245 | | | | | 250 | | | | | 255 | |
| Thr | Phe | Lys | Asn | Ala | Lys | Leu | Tyr | Gly | Pro | Asp | Val | Gly | Gln | Pro | Arg |
| | | | 260 | | | | | 265 | | | | | 270 | | |
| Arg | Lys | Thr | Ala | Lys | Met | Leu | Lys | Ser | Phe | Leu | Lys | Ala | Gly | Gly | Glu |
| | | 275 | | | | | 280 | | | | | 285 | | | |
| Val | Ile | Asp | Ser | Val | Thr | Trp | His | His | Tyr | Tyr | Leu | Asn | Gly | Arg | Thr |
| | 290 | | | | | 295 | | | | | 300 | | | | |
| Ala | Thr | Arg | Glu | Asp | Phe | Leu | Asn | Pro | Asp | Val | Leu | Asp | Ile | Phe | Ile |
| 305 | | | | | 310 | | | | | 315 | | | | | 320 |
| Ser | Ser | Val | Gln | Lys | Val | Phe | Gln | Val | Val | Glu | Ser | Thr | Arg | Pro | Gly |
| | | | | 325 | | | | | 330 | | | | | 335 | |
| Lys | Lys | Val | Trp | Leu | Gly | Glu | Thr | Ser | Ser | Ala | Tyr | Gly | Gly | Gly | Ala |
| | | | 340 | | | | | 345 | | | | | 350 | | |
| Pro | Leu | Leu | Ser | Asp | Thr | Phe | Ala | Ala | Gly | Phe | Met | Trp | Leu | Asp | Lys |
| | | 355 | | | | | 360 | | | | | 365 | | | |
| Leu | Gly | Leu | Ser | Ala | Arg | Met | Gly | Ile | Glu | Val | Val | Met | Arg | Gln | Val |
| | 370 | | | | | 375 | | | | | 380 | | | | |

```
Phe Phe Gly Ala Gly Asn Tyr His Leu Val Asp Glu Asn Phe Asp Pro
385                 390                 395                 400

Leu Pro Asp Tyr Trp Leu Ser Leu Leu Phe Lys Lys Leu Val Gly Thr
                405                 410                 415

Lys Val Leu Met Ala Ser Val Gln Gly Ser Lys Arg Arg Lys Leu Arg
            420                 425                 430

Val Tyr Leu His Cys Thr Asn Thr Asp Asn Pro Arg Tyr Lys Glu Gly
        435                 440                 445

Asp Leu Thr Leu Tyr Ala Ile Asn Leu His Asn Val Thr Lys Tyr Leu
    450                 455                 460

Arg Leu Pro Tyr Pro Phe Ser Asn Lys Gln Val Asp Lys Tyr Leu Leu
465                 470                 475                 480

Arg Pro Leu Gly Pro His Gly Leu Leu Ser Lys Ser Val Gln Leu Asn
                485                 490                 495

Gly Leu Thr Leu Lys Met Val Asp Asp Gln Thr Leu Pro Pro Leu Met
                500                 505                 510

Glu Lys Pro Leu Arg Pro Gly Ser Ser Leu Gly Cys Gln Leu Ser His
            515                 520                 525

Ile Val Phe Leu
    530
```

<210> SEQ ID NO: 16
<211> LENGTH: 1380
<212> TYPE: DNA
<213> ORGANISM: Mus musculus
<220> FEATURE:
<221> NAME/KEY: CDS
<222> LOCATION: (1)..(1140)

<400> SEQUENCE: 16

```
acc tac tca aga agc tca gtg gac atg ctc tac agt ttt gcc aag tgc      48
Thr Tyr Ser Arg Ser Ser Val Asp Met Leu Tyr Ser Phe Ala Lys Cys
  1               5                  10                  15 tcg ggg tta gac ctg atc ttt ggt cta aat gcg tta cta gga acc cca      96
Ser Gly Leu Asp Leu Ile Phe Gly Leu Asn Ala Leu Leu Gly Thr Pro
             20                  25                  30 gac tta cgg tgg aac agc tcc aac gcc cag ctt ctc ctt gac tac tgc     144
Asp Leu Arg Trp Asn Ser Ser Asn Ala Gln Leu Leu Leu Asp Tyr Cys
         35                  40                  45 tct tcc aag ggt tat aac atc tcc tgg gaa ctg gca aat gag ccc aac     192
Ser Ser Lys Gly Tyr Asn Ile Ser Trp Glu Leu Ala Asn Glu Pro Asn
     50                  55                  60 agt ttc tgg aag aaa gct cac att ctc atc gat ggg ttg cag tta gga     240
Ser Phe Trp Lys Lys Ala His Ile Leu Ile Asp Gly Leu Gln Leu Gly
 65                  70                  75                  80 gaa gac ttt gtg gag ttg cat aaa ctt cta caa agg tca gct ttc caa     288
Glu Asp Phe Val Glu Leu His Lys Leu Leu Gln Arg Ser Ala Phe Gln
                 85                  90                  95 aat gca aaa ctc tat ggt cct gac atc ggt cag cct cga ggg aag aca     336
Asn Ala Lys Leu Tyr Gly Pro Asp Ile Gly Gln Pro Arg Gly Lys Thr
            100                 105                 110 gtt aaa ctg ctg agg agt ttc ctg aag gct ggc gga gaa gtg atc gac     384
Val Lys Leu Leu Arg Ser Phe Leu Lys Ala Gly Gly Glu Val Ile Asp
        115                 120                 125 tct ctt aca tgg cat cac tat tac ttg aat gga cgc atc gct acc aaa     432
Ser Leu Thr Trp His His Tyr Tyr Leu Asn Gly Arg Ile Ala Thr Lys
    130                 135                 140 gaa gat ttt ctg agc tct gat gtg ctg gac act ttt att ctc tct gtg     480
```

```
                                       -continued

Glu Asp Phe Leu Ser Ser Asp Val Leu Asp Thr Phe Ile Leu Ser Val
145                 150                 155                 160 caa aaa att ctg aag gtc act aaa gag atc aca cct ggc aag aag gtc      528
Gln Lys Ile Leu Lys Val Thr Lys Glu Ile Thr Pro Gly Lys Lys Val
                165                 170                 175 tgg ttg gga gag acg agc tca gct tac ggt ggc ggt gca ccc ttg ctg      576
Trp Leu Gly Glu Thr Ser Ser Ala Tyr Gly Gly Gly Ala Pro Leu Leu
            180                 185                 190 tcc aac acc ttt gca gct ggc ttt atg tgg ctg gat aaa ttg ggc ctg      624
Ser Asn Thr Phe Ala Ala Gly Phe Met Trp Leu Asp Lys Leu Gly Leu
        195                 200                 205 tca gcc cag atg ggc ata gaa gtc gtg atg agg cag gtg ttc ttc gga      672
Ser Ala Gln Met Gly Ile Glu Val Val Met Arg Gln Val Phe Phe Gly
    210                 215                 220 gca ggc aac tac cac tta gtg gat gaa aac ttt gag cct tta cct gat      720
Ala Gly Asn Tyr His Leu Val Asp Glu Asn Phe Glu Pro Leu Pro Asp
225                 230                 235                 240 tac tgg ctc tct ctt ctg ttc aag aaa ctg gta ggt ccc agg gtg tta      768
Tyr Trp Leu Ser Leu Leu Phe Lys Lys Leu Val Gly Pro Arg Val Leu
                245                 250                 255 ctg tca aga gtg aaa ggc cca gac agg agc aaa ctc cga gtg tat ctc      816
Leu Ser Arg Val Lys Gly Pro Asp Arg Ser Lys Leu Arg Val Tyr Leu
            260                 265                 270 cac tgc act aac gtc tat cac cca cga tat cag gaa gga gat cta act      864
His Cys Thr Asn Val Tyr His Pro Arg Tyr Gln Glu Gly Asp Leu Thr
        275                 280                 285 ctg tat gtc ctg aac ctc cat aat gtc acc aag cac ttg aag gta ccg      912
Leu Tyr Val Leu Asn Leu His Asn Val Thr Lys His Leu Lys Val Pro
    290                 295                 300 cct ccg ttg ttc agg aaa cca gtg gat acg tac ctt ctg aag cct tcg      960
Pro Pro Leu Phe Arg Lys Pro Val Asp Thr Tyr Leu Leu Lys Pro Ser
305                 310                 315                 320 ggg ccg gat gga tta ctt tcc aaa tct gtc caa ctg aac ggt caa att     1008
Gly Pro Asp Gly Leu Leu Ser Lys Ser Val Gln Leu Asn Gly Gln Ile
                325                 330                 335 ctg aag atg gtg gat gag cag acc ctg cca gct ttg aca gaa aaa cct     1056
Leu Lys Met Val Asp Glu Gln Thr Leu Pro Ala Leu Thr Glu Lys Pro
            340                 345                 350 ctc ccc gca gga agt gca cta agc ctg cct gcc ttt tcc tat ggt ttt     1104
Leu Pro Ala Gly Ser Ala Leu Ser Leu Pro Ala Phe Ser Tyr Gly Phe
        355                 360                 365 ttt gtc ata aga gat gcc aaa att gct gct tgt ata tgaaaataaa          1150
Phe Val Ile Arg Asp Ala Lys Ile Ala Ala Cys Ile
    370                 375                 380 aggcatacgg taccctgag acaaaagccg aggggggtgt tattcataaa acaaaccct     1210 agtttaggag gccacctcct tgccgagttc cagagcttcg ggagggtggg gtacacttca   1270
gtattacatt cagtgtggtg ttctcctcta agaagaatac tgcaggtggt gacagttaat   1330
agcactgtgt ggcaaatgac gcttagccct ttgcatgcaa aaaaaaaaa               1380

<210> SEQ ID NO: 17
<211> LENGTH: 380
<212> TYPE: PRT
<213> ORGANISM: Mus musculus

<400> SEQUENCE: 17

Thr Tyr Ser Arg Ser Ser Val Asp Met Leu Tyr Ser Phe Ala Lys Cys
 1               5                  10                  15

Ser Gly Leu Asp Leu Ile Phe Gly Leu Asn Ala Leu Leu Gly Thr Pro
```

-continued

```
                        20                      25                      30
Asp Leu Arg Trp Asn Ser Ser Asn Ala Gln Leu Leu Asp Tyr Cys
             35                      40                      45

Ser Ser Lys Gly Tyr Asn Ile Ser Trp Glu Leu Gly Asn Glu Pro Asn
 50                      55                      60

Ser Phe Trp Lys Lys Ala His Ile Leu Ile Asp Gly Leu Gln Leu Gly
 65                      70                      75                      80

Glu Asp Phe Val Glu Leu His Lys Leu Leu Gln Arg Ser Ala Phe Gln
                     85                      90                      95

Asn Ala Lys Leu Tyr Gly Pro Asp Ile Gly Gln Pro Arg Gly Lys Thr
                    100                     105                     110

Val Lys Leu Leu Arg Ser Phe Leu Lys Ala Gly Gly Glu Val Ile Asp
                    115                     120                     125

Ser Leu Thr Trp His His Tyr Tyr Leu Asn Gly Arg Ile Ala Thr Lys
                    130                     135                     140

Glu Asp Phe Leu Ser Ser Asp Val Leu Asp Thr Phe Ile Leu Ser Val
145                     150                     155                     160

Gln Lys Ile Leu Lys Val Thr Lys Glu Ile Thr Pro Gly Lys Lys Val
                    165                     170                     175

Trp Leu Gly Glu Thr Ser Ser Ala Tyr Gly Gly Gly Ala Pro Leu Leu
                    180                     185                     190

Ser Asn Thr Phe Ala Ala Gly Phe Met Trp Leu Asp Lys Leu Gly Leu
                    195                     200                     205

Ser Ala Gln Met Gly Ile Glu Val Val Met Arg Gln Val Phe Phe Gly
                    210                     215                     220

Ala Gly Asn Tyr His Leu Val Asp Glu Asn Phe Glu Pro Leu Pro Asp
225                     230                     235                     240

Tyr Trp Leu Ser Leu Leu Phe Lys Lys Leu Val Gly Pro Arg Val Leu
                    245                     250                     255

Leu Ser Arg Val Lys Gly Pro Asp Arg Ser Lys Leu Arg Val Tyr Leu
                    260                     265                     270

His Cys Thr Asn Val Tyr His Pro Arg Tyr Gln Glu Gly Asp Leu Thr
                    275                     280                     285

Leu Tyr Val Leu Asn Leu His Asn Val Thr Lys His Leu Lys Val Pro
                    290                     295                     300

Pro Pro Leu Phe Arg Lys Pro Val Asp Thr Tyr Leu Leu Lys Pro Ser
305                     310                     315                     320

Gly Pro Asp Gly Leu Leu Ser Lys Ser Val Gln Leu Asn Gly Gln Ile
                    325                     330                     335

Leu Lys Met Val Asp Glu Gln Thr Leu Pro Ala Leu Thr Glu Lys Pro
                    340                     345                     350

Leu Pro Ala Gly Ser Ala Leu Ser Leu Pro Ala Phe Ser Tyr Gly Phe
                    355                     360                     365

Phe Val Ile Arg Asp Ala Lys Ile Ala Ala Cys Ile
                    370                     375                     380

<210> SEQ ID NO: 18
<211> LENGTH: 1191
<212> TYPE: DNA
<213> ORGANISM: Rattus sp.
<220> FEATURE:
<221> NAME/KEY: CDS
<222> LOCATION: (1)..(1140)

<400> SEQUENCE: 18
```

-continued

| | |
|---|---|
| acc tac tca cga agc tcg gtg gac atg ctc tac agt ttt gct aag tgc<br>Thr Tyr Ser Arg Ser Ser Val Asp Met Leu Tyr Ser Phe Ala Lys Cys<br>1               5                   10                  15 | 48 |
| tcg agg tta gac ctg atc ttt ggt cta aat gcg tta cta aga acc cca<br>Ser Arg Leu Asp Leu Ile Phe Gly Leu Asn Ala Leu Leu Arg Thr Pro<br>            20                  25                  30 | 96 |
| gac ttg cgg tgg aac agc tcc aac gcc cag ctt ctg ctc aac tac tgc<br>Asp Leu Arg Trp Asn Ser Ser Asn Ala Gln Leu Leu Leu Asn Tyr Cys<br>        35                  40                  45 | 144 |
| tct tcc aag ggt tat aac atc tgc tgg gaa ctg ggc aac gag ccc aac<br>Ser Ser Lys Gly Tyr Asn Ile Cys Trp Glu Leu Gly Asn Glu Pro Asn<br>50                  55                  60 | 192 |
| agt ttc tgg aag aaa gct cac att tcc atc gat ggg ttg cag cta gga<br>Ser Phe Trp Lys Lys Ala His Ile Ser Ile Asp Gly Leu Gln Leu Gly<br>65                  70                  75                  80 | 240 |
| gaa gac ttt gtg gag ttg cat aaa ctt cta caa aag tca gct ttc caa<br>Glu Asp Phe Val Glu Leu His Lys Leu Leu Gln Lys Ser Ala Phe Gln<br>                85                  90                  95 | 288 |
| aac gca aaa ctc tat ggt cct gac att ggt cag cct cga ggg aag aca<br>Asn Ala Lys Leu Tyr Gly Pro Asp Ile Gly Gln Pro Arg Gly Lys Thr<br>            100                 105                 110 | 336 |
| gtt aag ctg ctg aga agc ttc ctg aag gct ggt gga gaa gtg att gac<br>Val Lys Leu Leu Arg Ser Phe Leu Lys Ala Gly Gly Glu Val Ile Asp<br>        115                 120                 125 | 384 |
| tct ctc acc tgg cat cac tac tac ttg aat gga cga gtt gcg acc aaa<br>Ser Leu Thr Trp His His Tyr Tyr Leu Asn Gly Arg Val Ala Thr Lys<br>130                 135                 140 | 432 |
| gaa gat ttt ctg agc tct gat gtc ctg gac act ttt atc cta tct gtg<br>Glu Asp Phe Leu Ser Ser Asp Val Leu Asp Thr Phe Ile Leu Ser Val<br>145                 150                 155                 160 | 480 |
| caa aaa att ctg aag gtg act aag gag atg aca cct ggc aag aag gtc<br>Gln Lys Ile Leu Lys Val Thr Lys Glu Met Thr Pro Gly Lys Lys Val<br>                165                 170                 175 | 528 |
| tgg ttg gga gag acg agc tct gcc tac ggc ggc gga gcg ccc ttg ctg<br>Trp Leu Gly Glu Thr Ser Ser Ala Tyr Gly Gly Gly Ala Pro Leu Leu<br>            180                 185                 190 | 576 |
| tcc gat acc ttt gca gct ggc ttt atg tgg ctg gat aaa ttg ggc ctg<br>Ser Asp Thr Phe Ala Ala Gly Phe Met Trp Leu Asp Lys Leu Gly Leu<br>        195                 200                 205 | 624 |
| tca gcc cag ctg ggg ata gaa gtc gtg atg agg cag gtg ttt ttc gga<br>Ser Ala Gln Leu Gly Ile Glu Val Val Met Arg Gln Val Phe Phe Gly<br>210                 215                 220 | 672 |
| gca ggc aac tac cac tta gtg gac gaa aac ttc gag ccc ttg ccc gat<br>Ala Gly Asn Tyr His Leu Val Asp Glu Asn Phe Glu Pro Leu Pro Asp<br>225                 230                 235                 240 | 720 |
| tac tgg ctc tct ctc ctg ttc aag aaa ctg gta ggt ccc aag gtg tta<br>Tyr Trp Leu Ser Leu Leu Phe Lys Lys Leu Val Gly Pro Lys Val Leu<br>                245                 250                 255 | 768 |
| atg tca aga gtg aaa ggc cca gac aga agc aaa ctc cga gtg tac ctc<br>Met Ser Arg Val Lys Gly Pro Asp Arg Ser Lys Leu Arg Val Tyr Leu<br>            260                 265                 270 | 816 |
| cac tgc acg aac gtc tat cac cca agg tat cgg gaa gga gat tta act<br>His Cys Thr Asn Val Tyr His Pro Arg Tyr Arg Glu Gly Asp Leu Thr<br>        275                 280                 285 | 864 |
| ctg tac gtc ctg aac ctc cat aat gtc acc aag cac ttg aag ctg ccg<br>Leu Tyr Val Leu Asn Leu His Asn Val Thr Lys His Leu Lys Leu Pro<br>290                 295                 300 | 912 |
| cct ccg atg ttc agc aga ccg gtg gat aag tac ctg ctg aag cct ttc<br>Pro Pro Met Phe Ser Arg Pro Val Asp Lys Tyr Leu Leu Lys Pro Phe<br>305                 310                 315                 320 | 960 |

```
ggt tct gac gga ctg ctt tcc aaa tcc gtc caa ctg aac ggt caa acc       1008
Gly Ser Asp Gly Leu Leu Ser Lys Ser Val Gln Leu Asn Gly Gln Thr
                325                 330                 335 ctg aag atg gtc gat gag cag acc ctg cca gct cta aca gaa aaa cct       1056
Leu Lys Met Val Asp Glu Gln Thr Leu Pro Ala Leu Thr Glu Lys Pro
            340                 345                 350 ctc ccc gca gga agc tca cta agc gtg ccc gcc ttt tcc tat ggg ttt       1104
Leu Pro Ala Gly Ser Ser Leu Ser Val Pro Ala Phe Ser Tyr Gly Phe
                355                 360                 365 ttt gtc ata aga aat gcc aaa atc gca gct tgt ata tgaaataaa             1150
Phe Val Ile Arg Asn Ala Lys Ile Ala Ala Cys Ile
        370                 375             380 aggcttacag tacccctgaa aaaaaaaaaa aaaaaaaaaa a                          1191

<210> SEQ ID NO: 19
<211> LENGTH: 380
<212> TYPE: PRT
<213> ORGANISM: Rattus sp.

<400> SEQUENCE: 19

Thr Tyr Ser Arg Ser Ser Val Asp Met Leu Tyr Ser Phe Ala Lys Cys
  1               5                  10                  15

Ser Arg Leu Asp Leu Ile Phe Gly Leu Asn Ala Leu Leu Arg Thr Pro
             20                  25                  30

Asp Leu Arg Trp Asn Ser Ser Asn Ala Gln Leu Leu Leu Asn Tyr Cys
         35                  40                  45

Ser Ser Lys Gly Tyr Asn Ile Cys Trp Glu Leu Gly Asn Glu Pro Asn
     50                  55                  60

Ser Phe Trp Lys Lys Ala His Ile Ser Ile Asp Gly Leu Gln Leu Gly
 65                  70                  75                  80

Glu Asp Phe Val Glu Leu His Lys Leu Leu Gln Lys Ser Ala Phe Gln
                 85                  90                  95

Asn Ala Lys Leu Tyr Gly Pro Asp Ile Gly Gln Pro Arg Gly Lys Thr
            100                 105                 110

Val Lys Leu Leu Arg Ser Phe Leu Lys Ala Gly Gly Glu Val Ile Asp
        115                 120                 125

Ser Leu Thr Trp His His Tyr Tyr Leu Asn Gly Arg Val Ala Thr Lys
    130                 135                 140

Glu Asp Phe Leu Ser Ser Asp Val Leu Asp Thr Phe Ile Leu Ser Val
145                 150                 155                 160

Gln Lys Ile Leu Lys Val Thr Lys Glu Met Thr Pro Gly Lys Lys Val
                165                 170                 175

Trp Leu Gly Glu Thr Ser Ser Ala Tyr Gly Gly Gly Ala Pro Leu Leu
            180                 185                 190

Ser Asp Thr Phe Ala Ala Gly Phe Met Trp Leu Asp Lys Leu Gly Leu
        195                 200                 205

Ser Ala Gln Leu Gly Ile Glu Val Val Met Arg Gln Val Phe Phe Gly
    210                 215                 220

Ala Gly Asn Tyr His Leu Val Asp Glu Asn Phe Glu Pro Leu Pro Asp
225                 230                 235                 240

Tyr Trp Leu Ser Leu Leu Phe Lys Lys Leu Val Gly Pro Lys Val Leu
                245                 250                 255
```

```
Met Ser Arg Val Lys Gly Pro Asp Arg Ser Lys Leu Arg Val Tyr Leu
            260                 265                 270

His Cys Thr Asn Val Tyr His Pro Arg Tyr Arg Glu Gly Asp Leu Thr
            275                 280                 285

Leu Tyr Val Leu Asn Leu His Asn Val Thr Lys His Leu Lys Leu Pro
            290                 295                 300

Pro Pro Met Phe Ser Arg Pro Val Asp Lys Tyr Leu Lys Pro Phe
305             310                 315                 320

Gly Ser Asp Gly Leu Leu Ser Lys Ser Val Gln Leu Asn Gly Gln Thr
                325                 330                 335

Leu Lys Met Val Asp Glu Gln Thr Leu Pro Ala Leu Thr Glu Lys Pro
                340                 345                 350

Leu Pro Ala Gly Ser Ser Leu Ser Val Pro Ala Phe Ser Tyr Gly Phe
                355                 360                 365

Phe Val Ile Arg Asn Ala Lys Ile Ala Ala Cys Ile
            370                 375                 380
```

<210> SEQ ID NO: 20
<211> LENGTH: 18
<212> TYPE: DNA
<213> ORGANISM: Artificial Sequence
<220> FEATURE:
<223> OTHER INFORMATION: Description of Artificial Sequence:
      OLIGONUCLEOTIDE

<400> SEQUENCE: 20
aaaaagttca agaacagc                                                18

<210> SEQ ID NO: 21
<211> LENGTH: 17
<212> TYPE: DNA
<213> ORGANISM: Artificial Sequence
<220> FEATURE:
<223> OTHER INFORMATION: Description of Artificial Sequence:
      OLIGONUCLEOTIDE

<400> SEQUENCE: 21
cgaagctctg gaactcg                                                 17

<210> SEQ ID NO: 22
<211> LENGTH: 28
<212> TYPE: DNA
<213> ORGANISM: Artificial Sequence
<220> FEATURE:
<223> OTHER INFORMATION: Description of Artificial Sequence:
      OLIGONUCLEOTIDE

<400> SEQUENCE: 22
aactggaaga attcgcggcc gcaggaat                                     28

<210> SEQ ID NO: 23
<211> LENGTH: 15
<212> TYPE: PRT
<213> ORGANISM: Artificial Sequence
<220> FEATURE:
<223> OTHER INFORMATION: Description of Artificial Sequence: PEPTIDE

<400> SEQUENCE: 23

```
Val Gln Gly Ser Lys Arg Arg Lys Leu Arg Val Tyr Leu His Cys
 1               5                  10                  15
```